(12) United States Patent
Stuart et al.

(10) Patent No.: US 11,020,548 B2
(45) Date of Patent: *Jun. 1, 2021

(54) DOSE INDICATORS WITH A RESILIENT DEFORMABLE ELEMENT

(71) Applicant: KINDEVA DRUG DELIVERY L.P., St. Paul, MN (US)

(72) Inventors: Adam J. Stuart, Loughborough (GB); Peter D. Hodson, Breaston (GB)

(73) Assignee: Kindeva Drug Delivery L.P., St. Paul, MN (US)

( * ) Notice: Subject to any disclaimer, the term of this patent is extended or adjusted under 35 U.S.C. 154(b) by 200 days.

This patent is subject to a terminal disclaimer.

(21) Appl. No.: 16/154,470

(22) Filed: Oct. 8, 2018

(65) Prior Publication Data

US 2019/0038855 A1 Feb. 7, 2019

Related U.S. Application Data

(63) Continuation of application No. 14/426,246, filed as application No. PCT/US2013/057269 on Aug. 29, 2013, now Pat. No. 10,092,714.

(30) Foreign Application Priority Data

Sep. 6, 2012 (GB) ..................... 1215917

(51) Int. Cl.
*A61M 15/00* (2006.01)
*G06M 1/04* (2006.01)
*G06M 1/08* (2006.01)

(52) U.S. Cl.
CPC ...... *A61M 15/0073* (2014.02); *A61M 15/009* (2013.01); *A61M 15/0021* (2014.02); *G06M 1/041* (2013.01); *G06M 1/083* (2013.01)

(58) Field of Classification Search
None
See application file for complete search history.

(56) References Cited

U.S. PATENT DOCUMENTS 3,189,273 A * 6/1965 Hellen ................. G06M 1/041
235/117 R
3,302,834 A 2/1967 Alsop
(Continued)

FOREIGN PATENT DOCUMENTS

EP 0559757 9/1993
GB 1317315 5/1973
(Continued)

OTHER PUBLICATIONS

International Search Report for PCT International Application No. PCT/US2013/057269 dated Dec. 12, 2013, 3 pages.

*Primary Examiner* — Kathryn E Ditmer
(74) *Attorney, Agent, or Firm* — Mueting Raasch Group

(57) ABSTRACT

The present disclosure relates to a dose indicator for a pressure-actuated metered dose inhaler (pMDI) device. In an embodiment, the dose indicator comprises a chassis element having a viewing portion, a display element located within the chassis element, a resilient deformable element, and an indexing element having an axis, translation of the indexing element along its axis from a first position to a second position causing deformation of the resilient deformable element in the same direction as translation of the indexing element resulting in generally greater displacement of portions of the resilient deformable element nearer to the axis relative to portions thereof further from the axis, the displacement of the portions of the resilient deformable element in the same direction as translation of the indexing element inducing indexing of the display element from a (Continued)

current position to a subsequent position relative to the viewing portion of the chassis element.

19 Claims, 18 Drawing Sheets

(56) References Cited

U.S. PATENT DOCUMENTS

| | | | |
|---|---|---|---|
| 3,404,681 A | 10/1968 | Fowler | |
| 3,732,864 A | 5/1973 | Thompson | |
| 5,349,945 A * | 9/1994 | Wass | A61M 15/009 |
| | | | 128/200.14 |
| 5,421,482 A | 6/1995 | Garby | |
| 5,718,355 A * | 2/1998 | Garby | A61M 15/0075 |
| | | | 222/36 |
| 5,871,007 A * | 2/1999 | Clark, Jr. | A61M 15/009 |
| | | | 128/200.14 |
| 5,904,139 A | 5/1999 | Hauser | |
| 6,155,251 A | 12/2000 | Hauser | |
| 6,415,785 B1 * | 7/2002 | Stage | A61M 15/009 |
| | | | 128/200.12 |
| 6,481,438 B1 * | 11/2002 | Gallem | A61M 15/009 |
| | | | 128/200.14 |
| 6,659,307 B1 | 12/2003 | Stradella | |
| 6,679,251 B1 | 1/2004 | Gallem | |
| 6,752,153 B1 * | 6/2004 | Eckert | A61M 15/009 |
| | | | 128/200.23 |
| 7,341,057 B2 | 3/2008 | Scarrott | |
| 7,806,295 B2 | 10/2010 | Stradella | |
| 9,132,247 B2 | 9/2015 | Allsop | |
| 2004/0221840 A1 | 11/2004 | Stockman-Lamb | |
| 2007/0210102 A1 * | 9/2007 | Stradella | G06M 1/045 |
| | | | 222/36 |
| 2008/0041877 A1 * | 2/2008 | Stradella | G06M 1/083 |
| | | | 222/30 |
| 2009/0173346 A1 * | 7/2009 | Stuart | G06M 1/16 |
| | | | 128/203.12 |
| 2009/0320839 A1 | 12/2009 | Blacker | |
| 2010/0229855 A1 * | 9/2010 | Howgill | G06M 1/06 |
| | | | 128/200.23 |
| 2011/0266306 A1 * | 11/2011 | Laut | G06M 1/166 |
| | | | 222/36 |
| 2012/0103331 A1 * | 5/2012 | Laut | A61M 15/0081 |
| | | | 128/203.15 |
| 2012/0312301 A1 * | 12/2012 | Allsop | A61M 15/0075 |
| | | | 128/203.12 |
| 2014/0150778 A1 * | 6/2014 | Malhotra | A61M 15/0075 |
| | | | 128/200.23 |

FOREIGN PATENT DOCUMENTS

| | | |
|---|---|---|
| GB | 2061116 | 5/1981 |
| GB | 2233236 | 1/1991 |
| GB | 2240930 | 8/1991 |
| GB | 2322804 | 9/1998 |
| GB | 2372543 | 8/2002 |
| GB | 2385640 | 8/2003 |
| WO | WO 1985-01880 | 5/1985 |
| WO | WO 1992-09324 | 6/1992 |
| WO | WO 1993-24167 | 12/1993 |
| WO | WO 1996-03172 | 2/1996 |
| WO | WO 1998-52634 | 11/1998 |
| WO | WO 2002-091293 | 11/2002 |
| WO | WO 2006-110080 | 10/2006 |
| WO | WO 2006-119766 | 11/2006 |
| WO | WO 2006-126965 | 11/2006 |
| WO | WO 2006-126967 | 11/2006 |
| WO | WO 2007-103712 | 9/2007 |
| WO | WO 2007-124406 | 11/2007 |
| WO | WO 2008-025087 | 3/2008 |
| WO | WO 2008-121459 | 10/2008 |
| WO | WO 2010-125291 | 11/2010 |
| WO | WO 2011-071788 | 6/2011 |
| WO | WO-2013113899 A1 * 8/2013 ........ A61M 15/0073 |  |
| WO | WO 2013-188609 | 12/2013 |

* cited by examiner

DOSE INDICATORS WITH A RESILIENT DEFORMABLE ELEMENT

CROSS REFERENCE TO RELATED APPLICATIONS

This application is a continuation of U.S. patent application Ser. No. 14/426,246, filed Mar. 5, 2015, now allowed, which is a national stage filing under 35 U.S.C. 371 of PCT/US2013/057269, filed Aug. 29, 2013, which claims the benefit of United Kingdom Patent Application No. 1215917.4, filed Sep. 6, 2012, which is incorporated herein by reference in its entirety.

TECHNICAL FIELD OF THE INVENTION

The present invention relates to improvements in or relating to dose indicators, and is more particularly, although not exclusively, concerned with dose indicators for pressure-actuated metered dose inhaler (pMDI) devices.

BACKGROUND TO THE INVENTION

Patients that need to use inhalers, such as pMDI devices, regularly have long had the need to be able to monitor their inhaler usage, and regulators of medicines have started to specify that some indication of when an inhaler is reaching the end of its recommended number of actuations as well as when it has reached or exceeded that number is integrated into the inhaler product. Dose counters (providing an accurate count of the number of doses remaining) and dose indicators (providing an indication of the number of doses remaining) have been proposed for use with inhalers. Yet, to date not many of the proposed dose counters or indicators for pMDIs have reached the market in a pMDI product. In most dose counters and dose indicators, the display is typically advanced each time the inhaler device is used, and it is particularly important that they do not undercount the number of dispensed doses as, in extreme cases, the patient may rely on the count shown on the pMDI device to receive life-saving medication. In dose counters or dose indicators, it may be acceptable for advancement of the display to be triggered (initiated) before or after the dose has been delivered, so long as it is practically impossible for the patient to trigger it without dispensing a dose. However, some of these dose counters or dose indicators are designed to require electronics which increases the cost, prevents the user from washing the device, may have battery life issues and, in the case of dose counters, may have difficulty obtaining regulatory approval for their use. In addition, many of these dose counters and/or dose indicators are complex requiring large numbers of small mechanical parts which gives rise to high costs, difficulties in assembly, and the requirement for complex dimensional tolerances. The added cost has long been a disincentive to product developers to incorporate a dose counter into an inhaler. In some instances, the dose counters and dose indicators require a re-design of what has become a standard shape and size of pMDI to significantly larger, bulkier and more awkward shapes. In addition, the character size and legibility of the display of such devices can be poor, making it difficult for a user to read them.

Examples of pMDI inhalers or devices having either dose counters or dose indicators are described in GB-A-1317315, WO-A-93/24167, U.S. Pat. No. 7,806,295, U.S. Pat. No. 5,421,482, U.S. Pat. No. 6,679,251, WO-A-02/91293, GB-A-2385640, WO-A-2006/119766, WO-A-2006/126965 and WO-A2008/025087.

GB-A-1317315 discloses a dose indicator that can be mounted in a pMDI actuator and which comprises four sets of advancement teeth which are sprung-loaded together. GB-A-2385640 discloses a dose indicator which is mountable within a pMDI actuator and which uses sets of fine teeth to advance the indicator.

WO-A-93/24167 discloses a two-component dose indicator that is mounted at the top of a pMDI actuator. WO-A-2006/126965 discloses a top-mounted dose indicator. WO-A-2008/025087 also discloses a top-mounted pMDI dose indicator in which an indicator ring component bears integral spring arms.

U.S. Pat. No. 7,806,295 discloses a dose indicator driven by a flexible tab attached to a ring. U.S. Pat. No. 5,421,482 discloses a mechanical dose indicator driven round by a ring of flexible arms on a rigid plate. WO-A-2006/119766 discloses a pMDI dose indicator comprising a single component for use with an unconventional rotary metering valve; thereby requiring modifications to the pMDI inhaler unit or to the actuator in which it is mounted.

U.S. Pat. No. 6,679,251 discloses a bottom-mounted pMDI dose counter which incorporates two C-springs the serve both to reset the dose counter and to provide follow-through for the valve firing of the inhaler. WO-A-02/91293 discloses a counter mechanism operated by a collapsible flexible 'spider'.

SUMMARY OF THE INVENTION

Each of the dose indicators or dose counters described above tends to involve features that would build expense into the finished design and cannot be considered suitable for use in price-sensitive markets.

One drawback with existing dose indicators is the number of components required for their construction. In some cases, there may be in excess of six components in the dose indicator. This tends to make such dose indicators expensive to manufacture both in terms of component cost and overall material cost. In addition, due to the number of components, there are substantial assembly costs.

Another drawback is the stack-up of dimensional tolerances of the components of the dose indicator. If many components are required to manufacture the dose indicator, the tolerance of each component needs to more predictable to ensure that the dose indicator operates as intended. This involves significant development time to optimise the dimensions and means that the number of components has an effect on the accuracy and reliability of the dose indicator during operation. There are also issues with combining components that have dimensions at the edge of tolerance, to ensure that the total stack of tolerances does not impede performance and that acceptable combinations are not unduly rejected. There are also issues with combining components that are at the edge of tolerance, to ensure that the total stack of tolerances does not impede performance and that acceptable combinations are not unduly rejected. There are also issues with combining components that are at the edge of tolerance, to ensure that the total stack of tolerances does not impede performance and that acceptable combinations are not unduly rejected.

The issue of cost is a particular concern when considering dose indicators for highly price-sensitive markets, for example, Asia.

The present invention seeks to provide a dose indicator that can be manufactured at low cost so that it becomes an attractive proposition even in price-sensitive markets.

Here and in the following description, the term "dose indicator" is intended to refer to both dose counter devices and dose indicator devices.

It has been recognised that in order to provide a dose indicator that can be manufactured at low costs, it would be desirable to provide a dose indicator that has fewer components.

Further it is desirable to provide an inexpensive, simple and reliable dose indicator that would be compact in size so that it could, at the same time, be inserted or fitted into a housing of a typical commercial inhaler, in particular into an actuator of a pressure-actuated metered dispensing device of similar shape and comparable size to existing, commercial actuators.

In accordance with a first aspect of the present invention, there is provided a dose indicator for a pressure-actuated metered fluid dispensing device, the dose indicator comprising:
  a chassis element having a viewing portion;
  a display element located within the chassis element;
  a resilient deformable element; and
  an indexing element having an axis, translation of the indexing element along its axis from a first position to a second position causing deformation of the resilient deformable element in the same direction as translation of the indexing element resulting in generally greater displacement of portions of the resilient deformable element nearer to the axis relative to portions thereof further from the axis, the displacement of the portions of the resilient deformable element in the same direction as translation of the indexing element inducing indexing of the display element from a current position to a subsequent position relative to the viewing portion of the chassis element.

It is to be recognised that the phrase "resulting in generally greater displacement of portions of the resilient deformable element nearer to the axis relative to portions thereof further from the axis" is to be understood that, in each instance, a generally greater displacement occurs nearer to the axis than further away from the axis. Preferably, the outline shape of the resulting displacement of the resilient deformable element is symmetrical about the axis. More preferably, the resulting outline shape may be an inverted frustum of a cone.

In one embodiment of the invention, the elements of the dose indicator are advantageously formed in a maximum of three components. In another embodiment, the dose indicator advantageously comprises only two components. By substantially reducing the number of components, the overall cost of a dose indicator in accordance with the present invention is substantially reduced. In addition, a dose indicator in accordance with the present invention can simply be slotted over a nozzle block in an actuator for a pressure-actuated metered dispensing device.

Preferably, the resilient deformable element is arranged around the axis of the indexing element. Ideally, the display element is also arranged around the axis of the indexing element. By having the resilient deformable element and the display element arranged around the axis of the indexing element, the components can easily be aligned with respect to the actuator in which the dose indicator is to be located and with respect to the associated pressure-actuated metered dispensing device. Preferably, the dose indicator is designed such that, when it is assembled into a pressure-actuated metered fluid dispensing device, the axis of the indexing element coincides with the central vertical axis of a stem socket or nozzle block of the pressure-actuated metered fluid dispensing device.

The display element may comprise a continuous display ring or a discontinuous display ring. By having the display element in the form of a display ring, the dose indicator can easily be indexed with respect to the housing in which it is located.

In one embodiment, the display element may comprise a disc centred about the axis of the indexing element. Again, this provides inherent alignment of the display element with respect to the indexing element.

Preferably, the indexing element comprises a tube element connected to the resilient deformable element.

Advantageously, the resilient deformable element comprises a grille element. A further grille element may be located adjacent the resilient deformable grille element so that it substantially abuts the resilient deformable grille element in the first position to restrict the passage of air through the abutting grille elements.

When the indexing element is in the second position, the resilient deformable grille element is spaced from the further grille element to allow the passage of air through the spaced apart grille elements. The cooperation between the deformable grille element and the further grille element advantageously ensures that the user is able to coordinate their inspiratory breath with their actuation of the pressure-actuated metered dispensing device. Moreover, such embodiments advantageously allow for the provision of a dose indicator that includes breath coordination functionality without increasing the overall cost of the dose indicator.

The further grille element may be associated with one of: the display element and the chassis element. In this case, the resilient deformable grille element is preferably associated with the other one of: the display element and the chassis element.

In one embodiment of the present invention, the chassis element may comprise a housing including a base portion and a lid portion, the base portion including the indexing element and the resilient deformable grille element. The lid portion is desirably connected to the base portion by a living hinge and is closable with respect to the base portion. This arrangement of the chassis element provides an effectively self-contained unit that can simply be inserted into an actuator of the pressure-actuated metered dispensing device, fitting into position over a stem socket or nozzle block in the housing.

Preferably, the base portion comprises a wall portion having the viewing portion formed therein. This viewing portion is desirably aligned with a window provided in the actuator of the pressure-actuated metered device when the dose indicator is inserted therein.

Advantageously, the housing forming the chassis is formed as one component.

In one embodiment, the display element may comprise the further grille element mentioned supra and be housed within the housing. The further grille element may be substantially rigid or it may be fixed. A rack may be formed on a portion of the display element by which it is indexed with respect to the viewing portion.

Advantageously, in embodiments in which the display element comprises the further grille element, the display element and further grille element are formed as one component.

In order to implement the indexing of the display element with respect to the viewing portion, desirably the housing further comprises a worm element arranged to engage with the rack formed on the display element, rotation of the worm element indexing the display element with respect to the viewing portion.

It is preferred that the worm element comprises a plurality of teeth located on at least a portion thereof. The worm element may comprise an axle portion at each end, the plurality of teeth being located between the two axle portions. Advantageously, a locking pawl is provided for engaging with at least one tooth formed on the worm element.

Ideally, the worm element is supported by first and second support members formed on the chassis element, the first and second support members advantageously being integrally formed with the lid portion. Advantageously, the first and second support members each have a through-hole to receive an end of the worm element, the through-holes being moulded using an injection moulding tool that opens along an axis substantially perpendicular to an axis defined by the centres of the through-holes.

Advantageously in those embodiments including a base portion, an advancement arm is provided in the base portion which is operable to rotate the worm element as the indexing element moves between the first and second positions. Preferably, the advancement arm and the base portion are integrally formed.

The spacing of the rack preferably corresponds to the flight of the worm element.

In a further embodiment, the lid portion may include at least one additional spring arm that engages with a hole provided in the side of the indexing element. This provides a restorative upward force to the resilient deformable element even in its rest position.

In alternative embodiments to those where the chassis element comprises a housing including a base portion and a lid portion, the base portion including the indexing element and the resilient deformable grille element, the chassis element may favourably comprise an inner wall portion and an outer wall portion joined by a rim portion, the inner and outer wall portions defining an annulus therebetween, the display element being mounted within the annulus with a portion of the display element being visible through the viewing portion formed in the outer wall portion.

Preferably, the chassis element includes a first set of chassis element teeth located within the annulus adjacent the rim portion and a second set of chassis element teeth associated with the outer wall portion and spaced from the rim portion. In addition, the outer wall portion may comprise a plurality of clip elements extending therefrom on which the second set of chassis element teeth is formed. Moreover, the first and second sets of chassis element teeth face one another and are integrally formed with the chassis element. Advantageously, the first and second sets of chassis element teeth are offset with respect to one another. In a similar way to the other embodiments, the chassis element is advantageously formed as one component.

In such embodiments, the display element may comprise first and second sets of display element teeth located on respective peripheral edges thereof, the first and second sets of chassis element teeth engaging with respective ones of the first and second sets of display element teeth in accordance with the first and second positions of the indexing element. In such embodiments, the display element may comprise the resilient deformable grille element and the indexing element, the resilient deformable grille element connecting the display element to the indexing element.

The display element is preferably formed as one component.

In addition, in such embodiments, translation of the indexing element to the second position favourably causes engagement of the second set of chassis element teeth with the second set of display element teeth to rotate the display element through a fraction of an indexing pitch in a first direction, and translation of the indexing element back to the first position causes engagement of the first set of chassis element teeth with the first set of display element teeth to rotate the display element through a remaining fraction of the indexing pitch in the first direction.

In such embodiments, the chassis element may further comprise a chassis element spring arranged to maintain engagement of the first set of chassis element teeth with the first set of display element teeth when the indexing element is in the first position. In addition, the chassis element spring may comprise the further grille element, the chassis element spring being connected to the inner wall portion.

In accordance with another aspect of the present invention, there is provided a pressure-actuated metered dispensing device comprising: an actuator portion; a window formed in the actuator portion; a dispensing portion; a nozzle block located between the actuator portion and the dispensing portion; a dose indicator as described above, the indexing element being aligned with the nozzle block and the viewing portion being aligned with the window in the actuator portion; and a canister comprising a container and a metering valve housed within the actuator portion, the metering valve having a valve stem that engages the nozzle block and wherein, in use, relative movement of the container and the nozzle block causes the translation of the indexing element from the first to the second position as a result of engagement of a portion of the canister and the indexing element.

BRIEF DESCRIPTION OF THE DRAWINGS

For a better understanding of the present invention, reference will now be made, by way of example only, to the accompanying drawings in which.

DETAILED DESCRIPTION OF THE INVENTION

Figure 1:
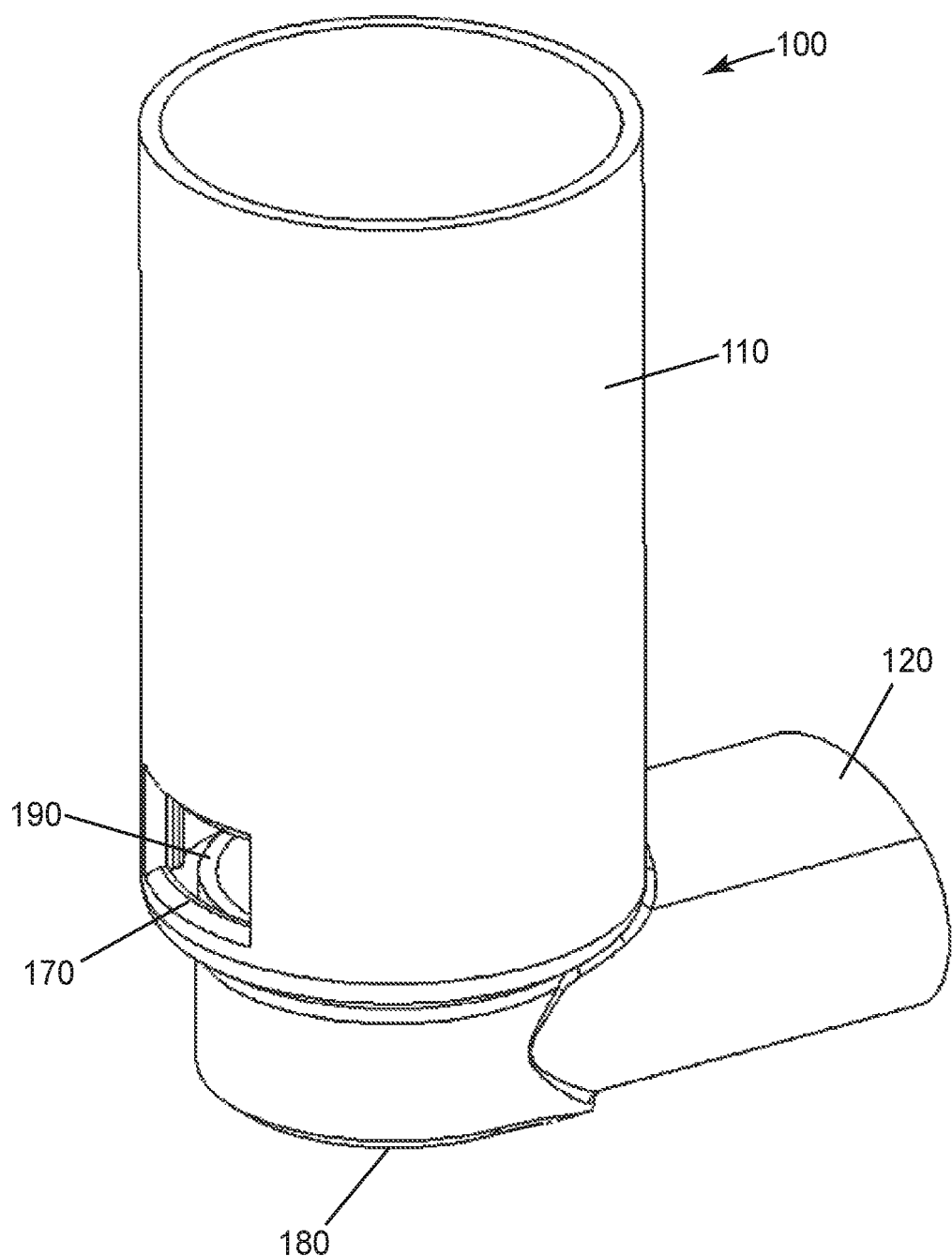
FIG. 1 illustrates an isometric top view of an exemplary actuator for a pMDI inhaler without a dose indicator.

The present invention will be described with respect to particular exemplary embodiments and with reference to certain drawings but the invention is not limited thereto. The drawings described are only schematic and are non-limiting. In the drawings, for illustrative purposes the size of some of the elements may be exaggerated and not drawn to scale.

It will be understood that the terms "vertical", "horizontal", "top", "bottom", "above", "below", "left", "right" etc. as used herein refer to particular orientations of the Figures and these terms are not limitations to the specific embodiments described herein.

As mentioned above, in addition to reducing the cost of a dose indicator for use with pMDI inhalers, it is desirable to provide a dose indicator that includes breath coordination functionality without increasing the overall cost of the dose indicator. The exemplary dose indicators shown in FIGS. 4 to 31 include such breath coordination functionality. However as described below, if desired or needed, these dose indicators can be simply modified in such a manner that this functionality is removed, while still maintaining an advantageous inexpensive, simple and reliable dose indicator.

Before turning to the exemplary embodiments, breath actuation and coordination are described in the following paragraphs to ensure a proper understanding of the breath coordination functionality of the exemplary embodiments.

Many users of pMDI inhalers find it difficult to time correctly the moment at which they actuate their pMDI inhaler relative to the moment at which they start to inhale. Further, a significant number of other users do not realise that they have a problem with coordinating their in-breath with the actuation of the pMDI inhaler and therefore do not realise that they are not receiving an optimum dose each time. Naturally, not being able to have the correct coordination leads to not having optimum treatment as possibly a large percentage of each dose is not inhaled. Accordingly, there is a general ongoing need for many pMDI users to have an inhaler that maximises the dose of the particular drug being delivered to their lungs via their inhaled inspiratory breath.

There are currently two main solutions to this problem, namely, breath actuation where a triggering mechanism utilises the inhalation of a user to release the pMDI valve; and breath coordination where the inhalation and the release of the dose are timed to coincide in some other way. The former solution ("breath actuation systems") tends to involve complex (and therefore expensive) mechanisms, whilst the latter solution ("breath coordination systems") can be much simpler and therefore cheaper.

Many breath coordination systems fit into one of two categories: "can't inhale until press" and "can't press until inhale". The former category typically involves air passageways through the inhaler that only open when the user pushes down on the pMDI canister (the assembly comprising the container and metering valve). In the latter category, it is not possible to press the pMDI inhaler downwards until some mechanical obstruction has been removed as a consequence of inspiration (e.g. had been unblocked by movement of a breath-operated obstructive vane). Thus, inhalation by the patient effectively allows movement of the container to operate a dispensing valve associated with the container.

It should be appreciated that many prior art dose indicators are not compatible with the inspiratory systems mentioned above, nor provide a mechanism in themselves for breath actuation or coordination.

As will be explained in detail below, certain advantageous embodiments of dose indicators in accordance with the present invention include an integrated breath coordination system of the "can't inhale until press" type of operation. This operation will be described in more detail below.

Figure 2:
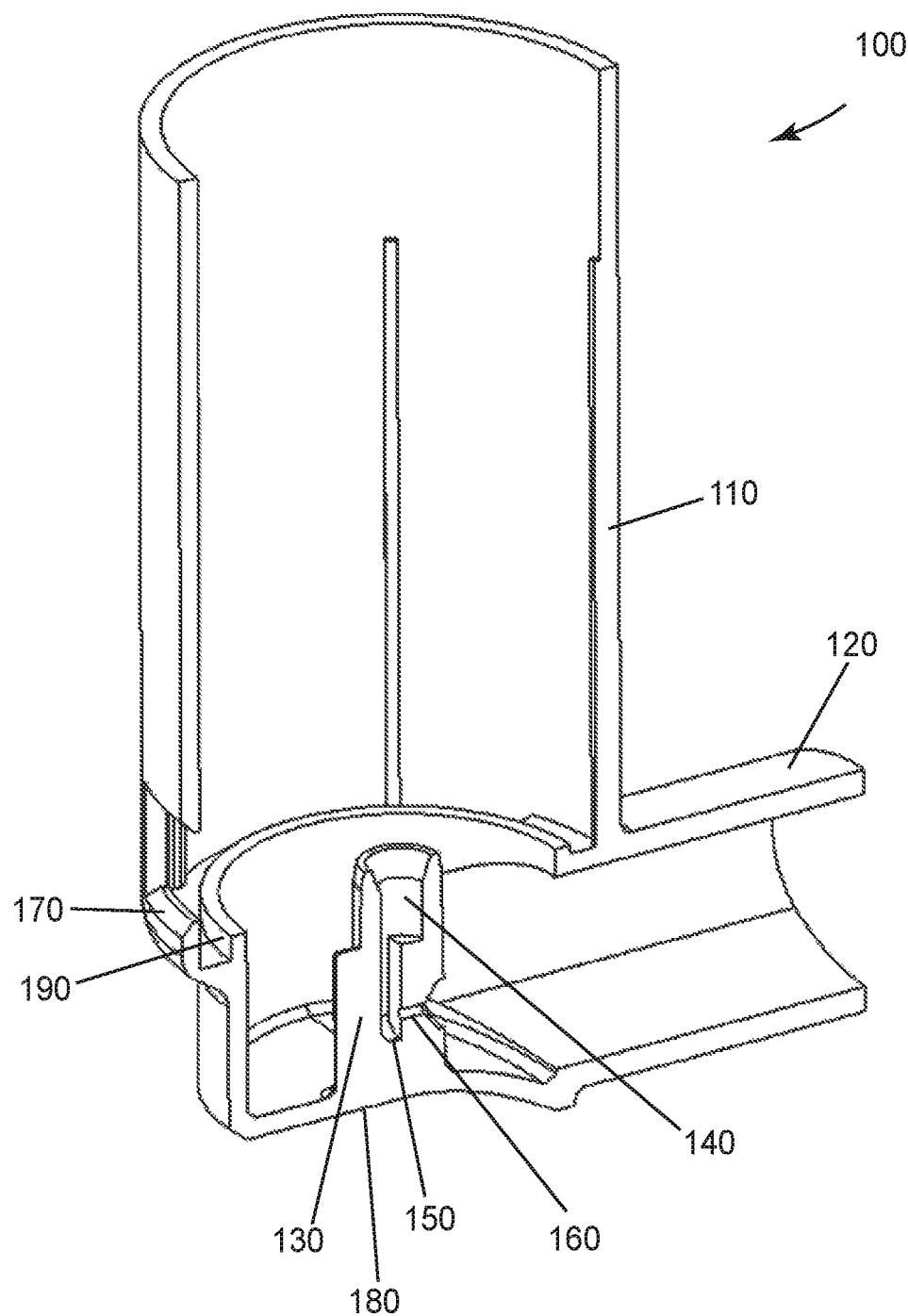
FIG. 2 is similar to FIG. 1 but illustrates an isometric sectioned top view of an exemplary actuator for a pMDI inhaler.

Referring initially to FIGS. 1 and 2, an exemplary actuator 100 for a pMDI inhaler (the inhalation canister not being shown) is shown. The actuator is similar in size and shape to many marketed pMDI actuators. The actuator 100 comprises a tubular housing portion 110 and a tubular mouthpiece portion 120. At the closed bottom end of the tubular housing portion 110 sits a nozzle block 130 that comprises a stem socket 140 in flow communication with a sump region 150 and an exit orifice 160. At the back of the tubular housing portion 110 is a viewing window 170. At the bottom of the actuator 100 is a thumb grip 180. An actuator running surface 190 is provided adjacent to the lower end of the tubular housing portion 110.

Figure 3:
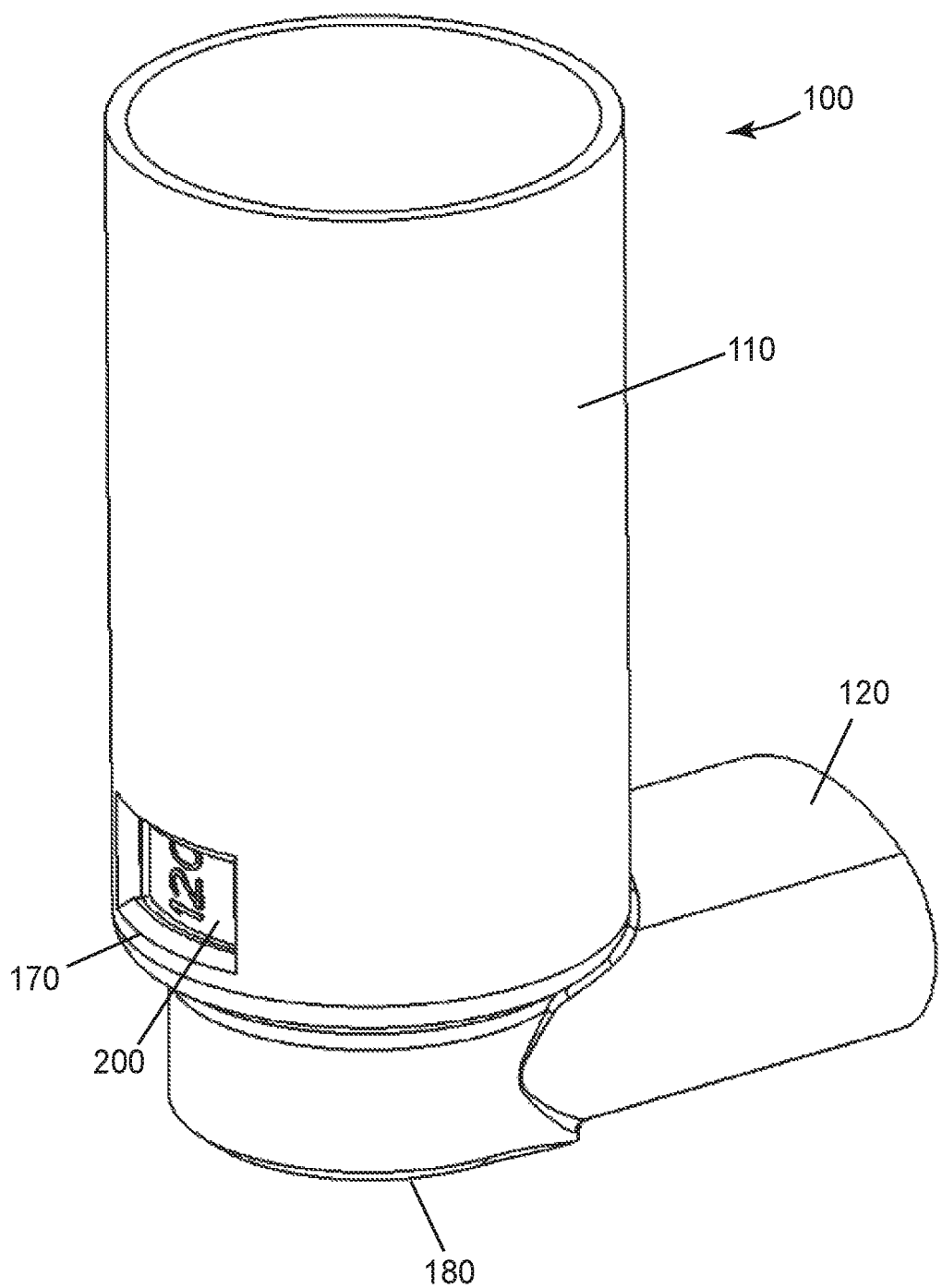
FIG. 3 is similar to FIG. 1 but illustrates an exemplary dose indicator of the present invention located within the actuator.

FIG. 3 is similar to FIG. 1 but illustrates a display element 200 that is visible through the viewing window 170 of the actuator 100. The display element 200 forms part of a dose indicator in accordance with the present invention. As will be described in more detail below, the display element may comprise a ring (not shown), in particular a continuous ring or a discontinuous ring, or alternatively a disc.

In accordance with a first exemplary embodiment of the present invention, the dose indicator 300 comprises three principal components, namely, a chassis element 310, a display element 320 and a worm element 330. It is intended for use with a pMDI inhaler actuator 100, for example, as described with reference to FIGS. 1 to 3 above, and a pMDI canister as will be described in more detail below with respect to FIG. 14. The form and use of such a pMDI canister will be familiar to those skilled in the art.

Figure 4:
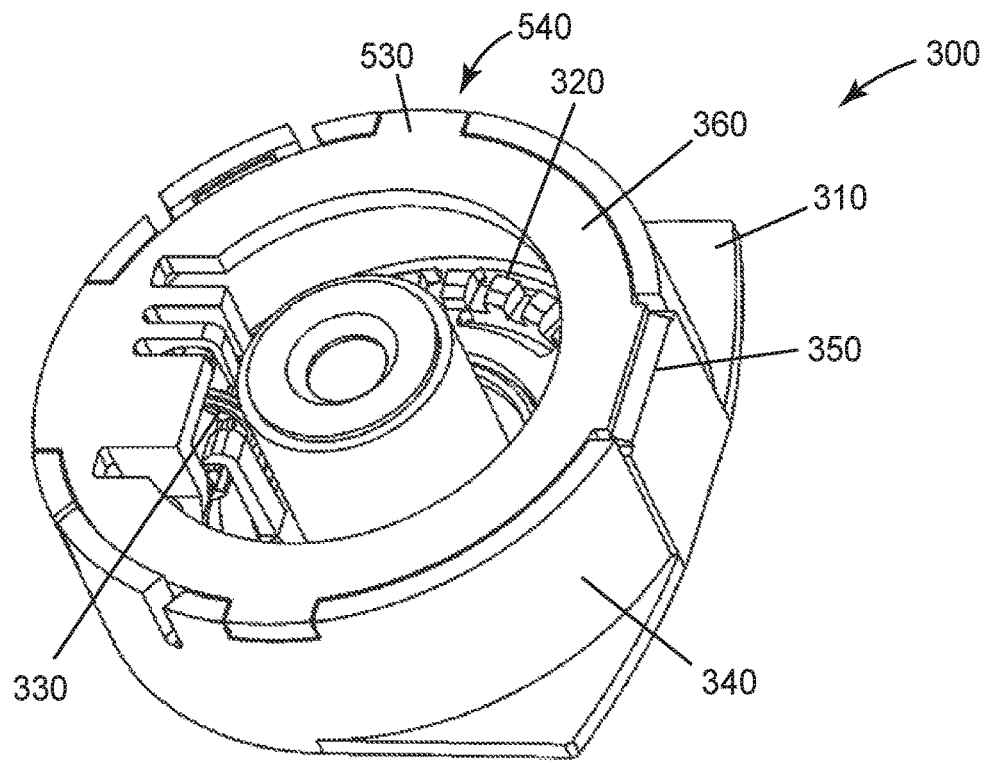
FIG. 4 illustrates an isometric top view of a dose indicator in accordance with a first exemplary embodiment of the present invention.

Referring now to FIGS. 4 to 12, the exemplary dose indicator 300 is shown in more detail. The chassis element 310 which has a generally rigid outer wall 340, joined via a living hinge 350 to a lid 360. At two points on the outer wall 340, flexible clips 370 are provided that serve to engage with two corresponding tabs 380 on the periphery of the lid 360. This engagement retains the lid in its closed position after assembly, as shown in FIG. 4. The underside 390 of the lid 360 also bears two support posts 400, 405 with lateral through-holes 410, 415 (FIG. 7) that serve as bearings for an axle 420 of the worm element 330. The support posts 400, 405 are angled outwardly towards their ends such that the through-holes 410, 415 may be injection moulded using tooling that needs no side-draw actions, thereby reducing moulding tool complexity and cost and minimising moulding cycle times. Between the two support posts 400, 415 is located a locking pawl 440 for engagement with the worm element 330.

Within the outer wall 340 is an annular resilient deformable grille element 450 that comprises a series of rings 460 linked by radial members 470. The rings 460 and radial members 470 define slots 480. The inside part of the annular resilient deformable grille element 450 extends upwards as a central alignment tube or a tubular indexing element 490, with a central aperture 500 in which may be located the hollow male stem of the pMDI valve (not shown) when the pMDI canister is assembled into the actuator 100 with the assembled dose indicator 300.

A hooked cantilevered advancement arm 510 is mounted near the inner edge (shown as 660 in FIG. 12) of the annular resilient deformable grille element 450 for engagement with the worm element 330 as will be described in more detail below. A viewing portion 520 in the form of a cut-out is provided in the outer wall 340 of the chassis element 310 through which the display element 320 can be seen when assembled. Further lid tabs 530 are provided which sit within respective recesses 540 formed in the outer wall 340 as is shown more clearly in FIG. 4.

Figure 8:
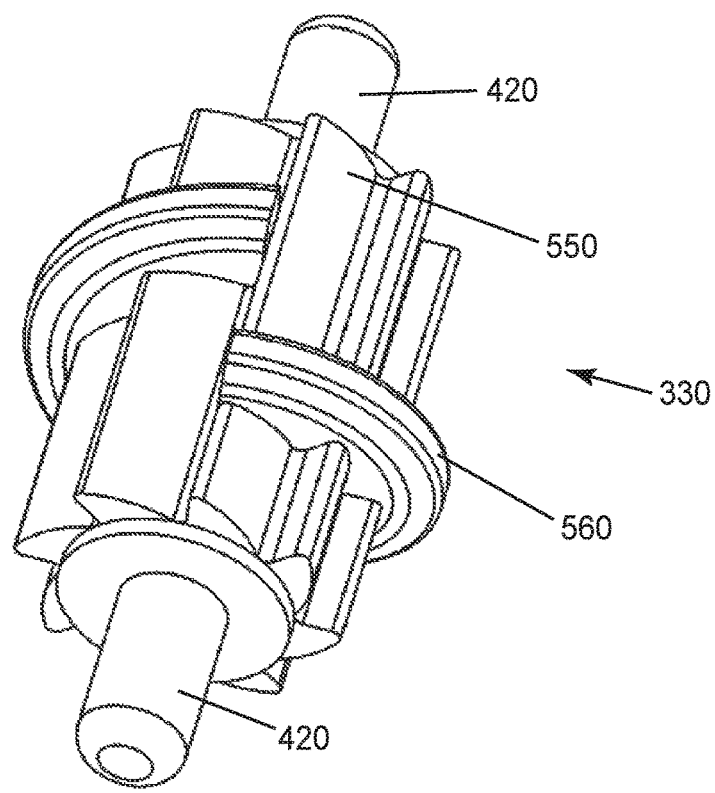
FIG. 8 illustrates an isometric top view of a worm element in accordance with the first exemplary embodiment of the present invention.

FIG. 8 illustrates the worm element 330 in more detail. As shown, the worm element 330 comprises a plurality of drive teeth 550 arranged around its periphery in a central region between the ends of the axle 420. In this exemplary embodiment, there are eight drive teeth 550 which are intersected by a single-turn worm flight 560 formed in a central portion of the worm element 330.

Figure 9:
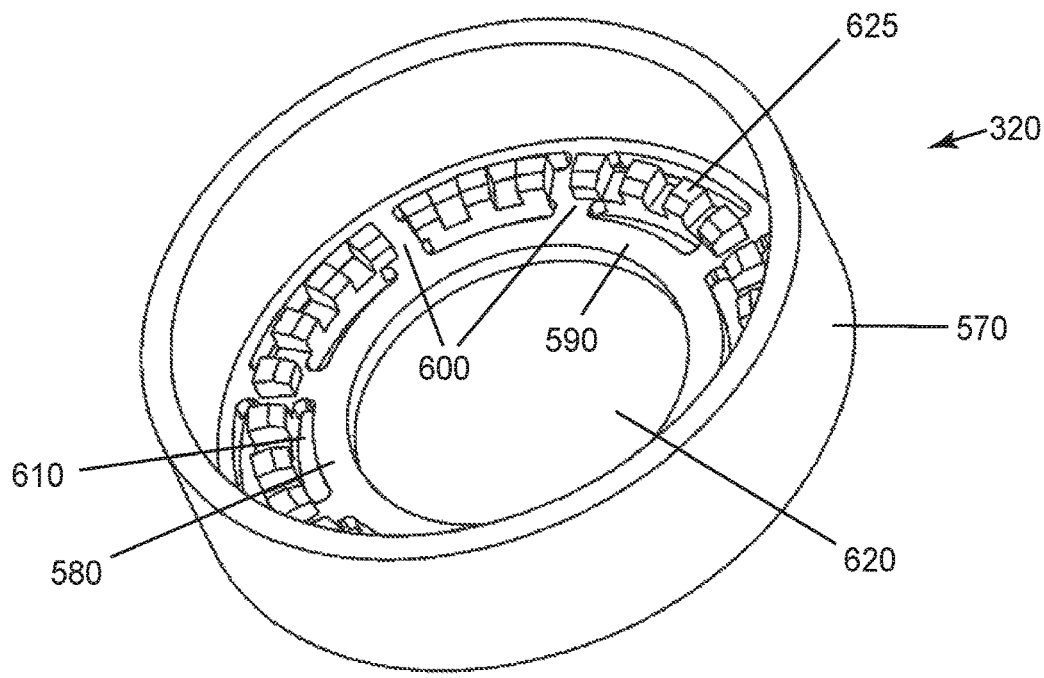
FIG. 9 illustrates an isometric top view of a display element in accordance with the first exemplary embodiment of the present invention (display numerals not being shown)

With reference to FIG. 9, the display element 320 comprises a display ring 570 in the form of a cylindrical tubular wall, the outside of which bears numerals (for example, 200, 190, 180; not shown) corresponding to the remaining number of doses of medicament in the container of the pMDI canister. Extending in from the bottom end of the display ring 570 is a substantially rigid grille element 580 in the form of rings 590 linked by radial members 600, the rings 590 and radial members 600 defining slots 610. A central aperture 620 is formed by the inner edge of the grille element 580. A series of teeth in the form of a rack 625 is mounted on the top surface of one ring of the grille element 580.

Figure 10:
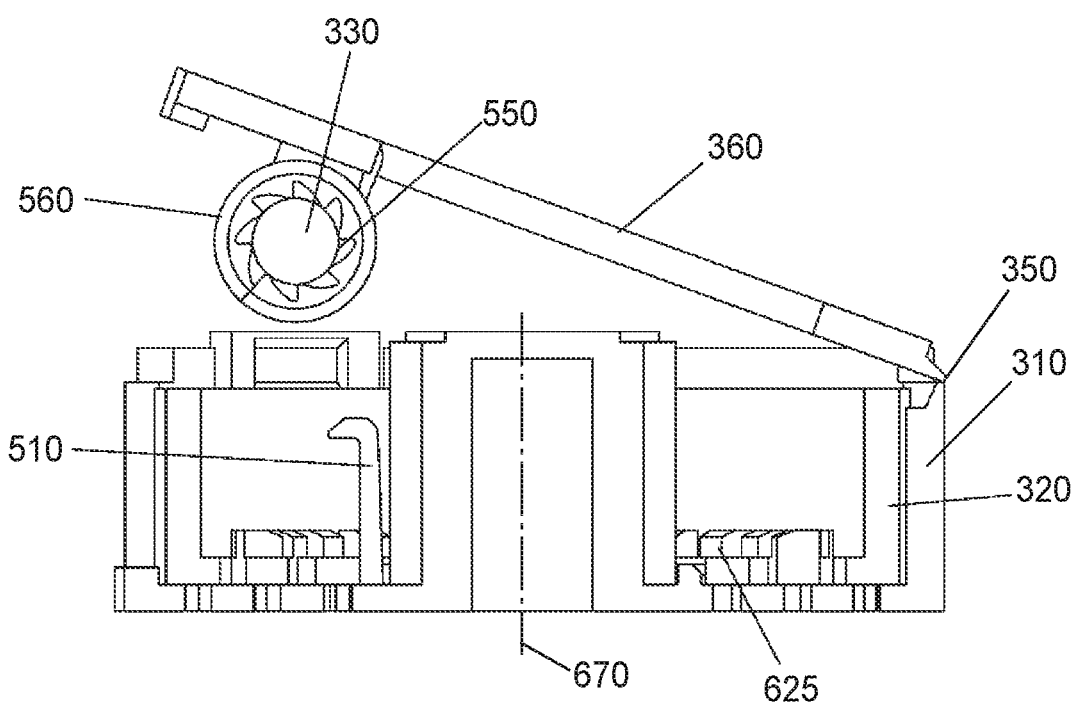
FIG. 10 illustrates a sectioned side view of the dose indicator in accordance with the first exemplary embodiment of the present invention with its lid partially open.
Figure 11:
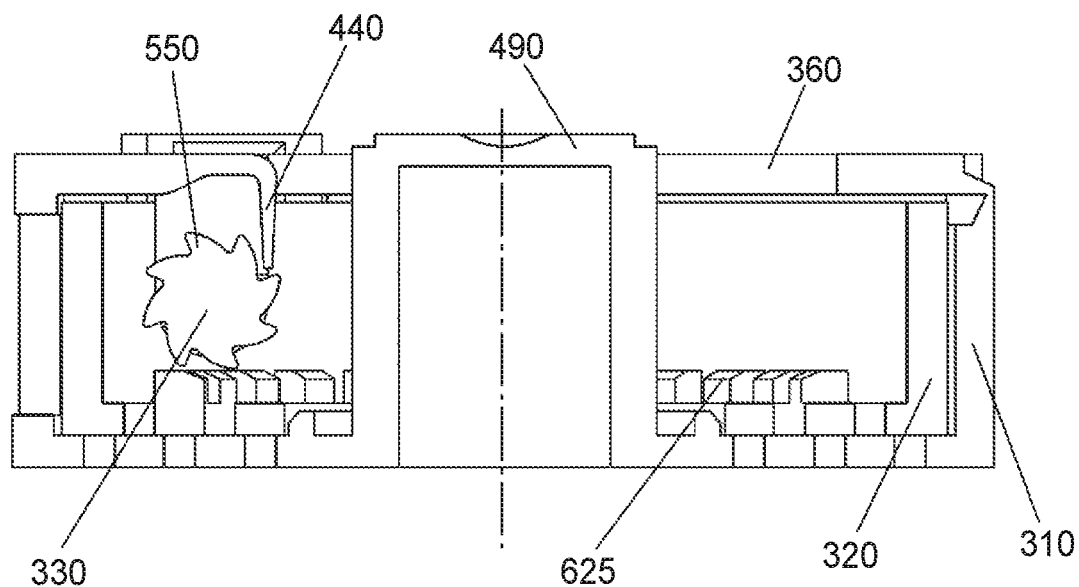
FIG. 11 illustrates a sectioned side view of the dose indicator in accordance with the first exemplary embodiment of the present invention with its lid closed.
Figure 12:
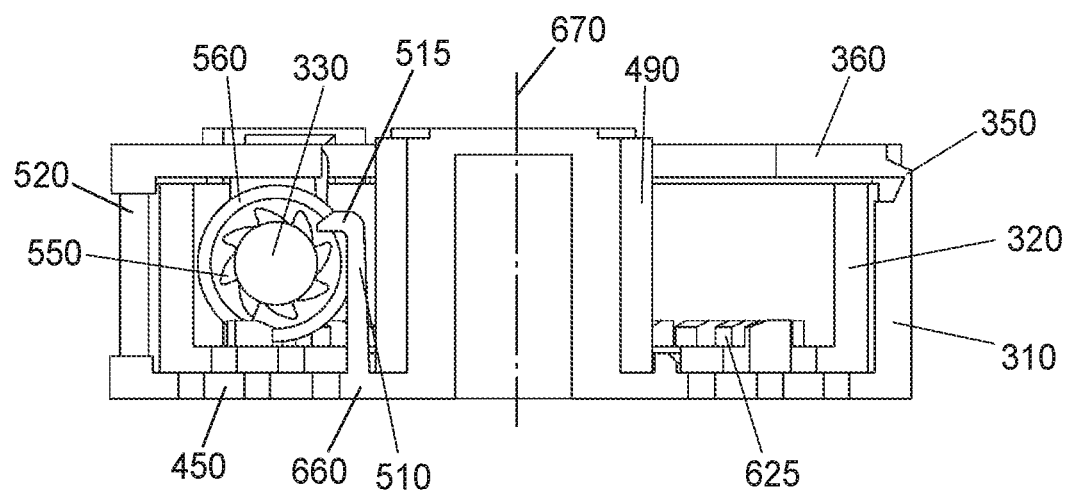
FIG. 12 illustrates another sectioned side view similar to that of FIG. 11, but illustrates the engagement of the worm element with an indexing arm.

FIGS. 5, 6 and 10 to 12 illustrate respective positions of the lid 360 with respect to the outer wall 340 as it is moved from an open position (FIGS. 5 and 6) to a fully closed position (FIGS. 11 and 12).

Figure 5:
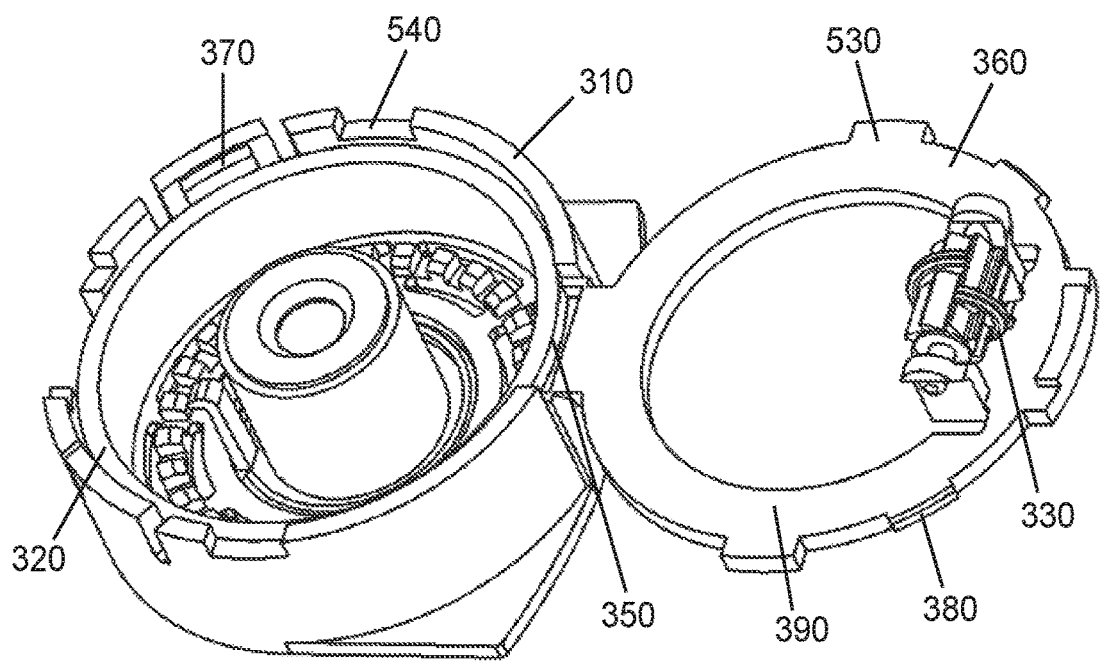
FIG. 5 illustrates an isometric top view of the dose indicator shown in FIG. 4 but with its lip open.

The exemplary dose indicator 300 is assembled as follows. Referring to FIGS. 4 to 9 in particular, the ends of the axle 420 of the worm element 330 are pushed into the through holes 410, 415 provided in respective ones of the two support posts 400, 405. This is done by pushing the worm element 330 towards the underside 390 of the lid 360 so that the support posts 400, 405 flex outwardly by a sufficient amount to allow the axle 420 to click into place within the through holes 410, 415, as shown in FIG. 5. The display element 320 is placed into the chassis element 310, as shown in FIG. 5, being pushed over the hooked end of the advancement arm 510, which transiently deflects inwardly to allow it to pass through the central aperture 620 in the grille element 580 of the display element 320. Care is taken to ensure, for example, by an automated vision recognition system and/or by the provision of alignment features (not shown), that the display element 320 is orientated correctly so that it displays the correct count numerals (e.g. "200") as seen through the viewing portion 520 of the chassis element 310. The dose indicator is now in the part-assembled state shown in FIGS. 5 and 6.

Figure 6:
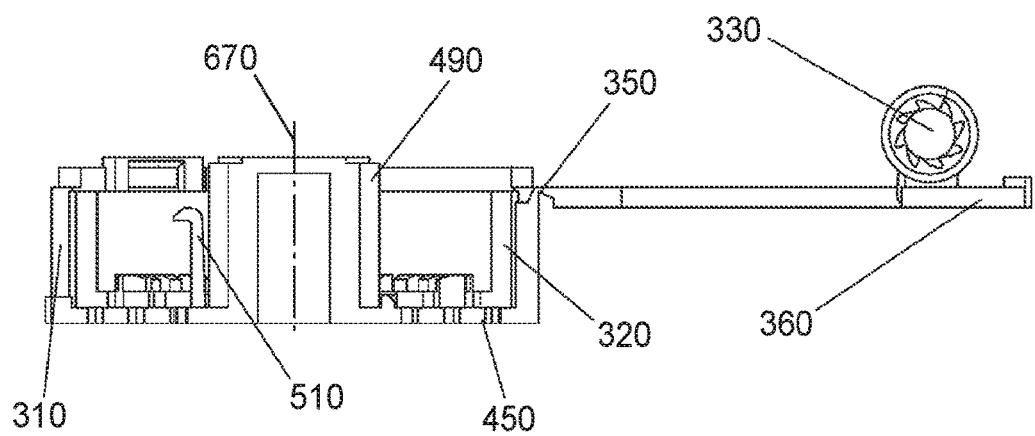
FIG. 6 illustrates a sectioned side view of the dose indicator shown in FIG. 5.
Figure 7:
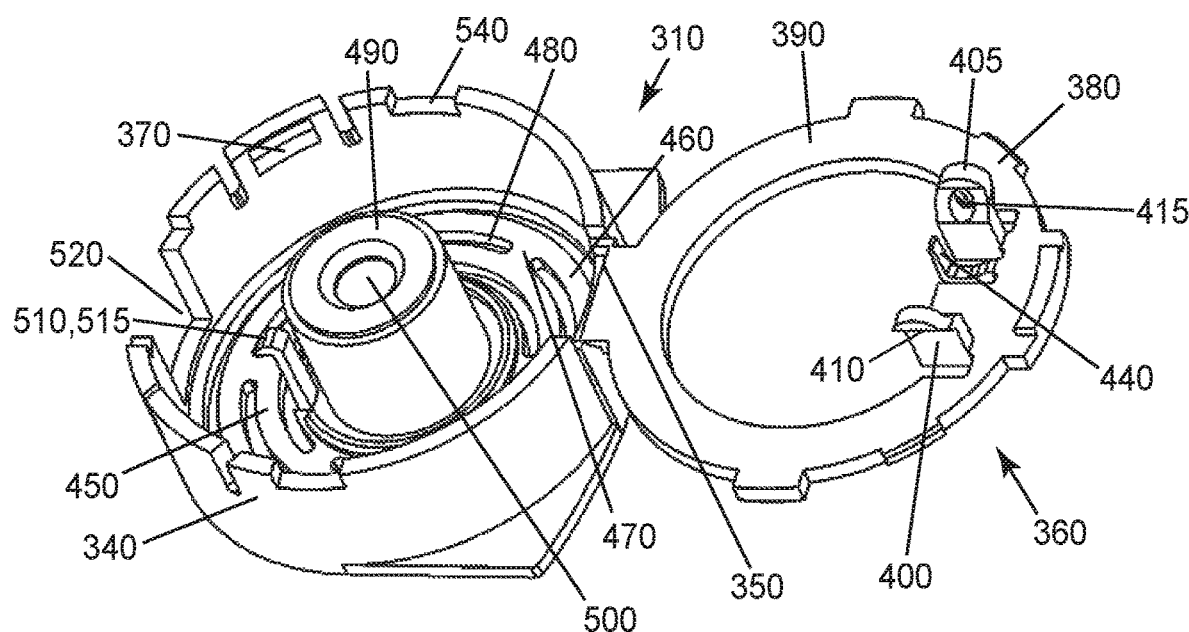
FIG. 7 illustrates a chassis element in accordance with the first exemplary embodiment of the present invention.

The final step of this very simple assembly procedure is to close the lid 360, as is shown in the sequence of FIGS. 5 and 6 (lid fully open), FIG. 10 (lid partially closed), and FIGS. 11 and 12 (lid fully closed). This movement of the lid 360 is made possible by the presence of the living hinge 350 that joins the lid 360 to the outer wall 340 of the chassis element 310. As the lid 360 reaches its fully closed position within the top of the outer wall 340, as shown also in FIG. 4, the lid tabs 380 formed on the lid 360 engage with the flexible clips 370 formed on the outer wall 340, thereby locking the lid 360 into its fully assembled position. In the fully assembled position, the two additional alignment tabs 530 on the lid 360 engage with corresponding recesses 540 in the top of the outer wall 340. The worm flight 560 of the worm element 330 is now engaged with the teeth of the rack 625 of the display element 320 as shown in FIGS. 12 and 13.

Use and operation of the exemplary dose indicator may best be understood with reference to FIGS. 11 to 17.

Figure 13:
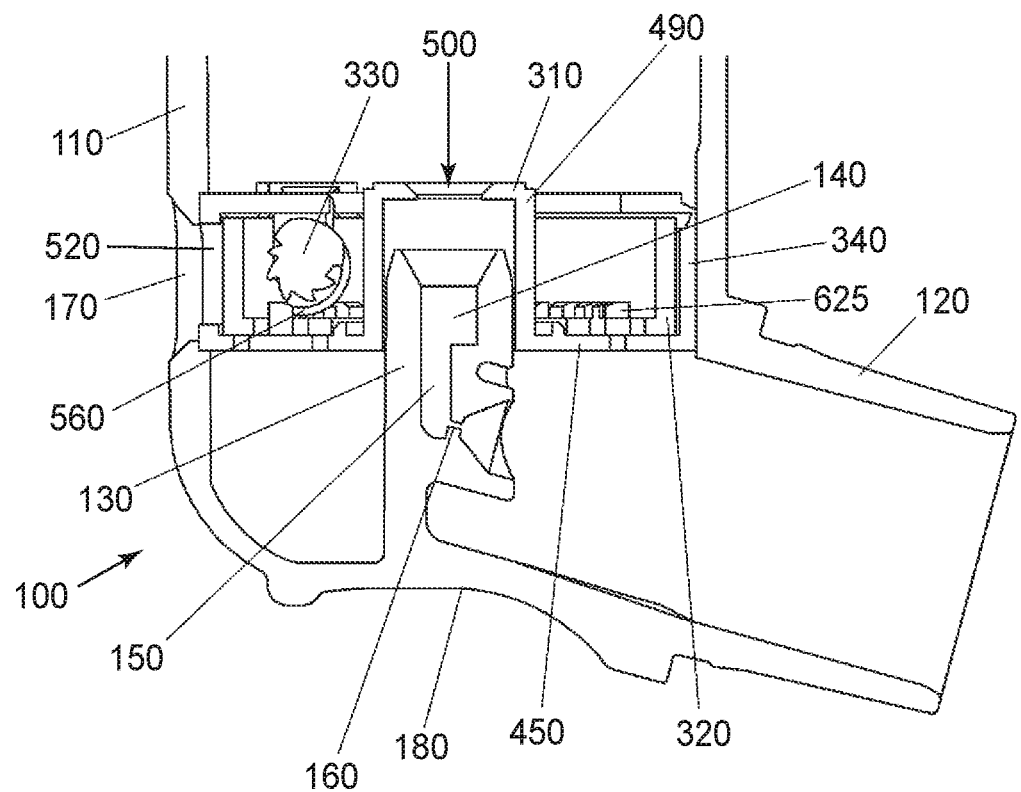
FIG. 13 illustrates a sectioned side view of the dose indicator in accordance with the first exemplary embodiment of the present invention mounted within a actuator of a pMDI inhaler.

Once assembled, the dose indicator 300 is then pushed into the actuator 100 and over the nozzle block 130 (FIG. 2), to reach the position shown in FIG. 13. As shown in FIG. 13, the outer wall 340 of the dose indicator 300 sits within the base of the tubular housing portion 110 of the actuator 100 with the viewing portion 520 of the outer wall 340 aligned with the window 170 of the actuator 100. Desirably, the window 170 is large enough for the user to see up to two sets of numerals, for example, '120' and '110', so that both are visible when the actual count corresponds to an intermediate number, for example, '116' or '115'. In this manner, the user can observe the shifted position of the display and can appreciate that the number of doses remaining has been decreased, for example, from one hundred and sixteen doses to a hundred and fifteen doses remaining. The indexing element 490 sits around the nozzle block 130 and is free to move axially upwards and downwards a certain distance with respect to the nozzle block 130 by virtue of the flexibility of the deformable grille element 450.

Figure 14:
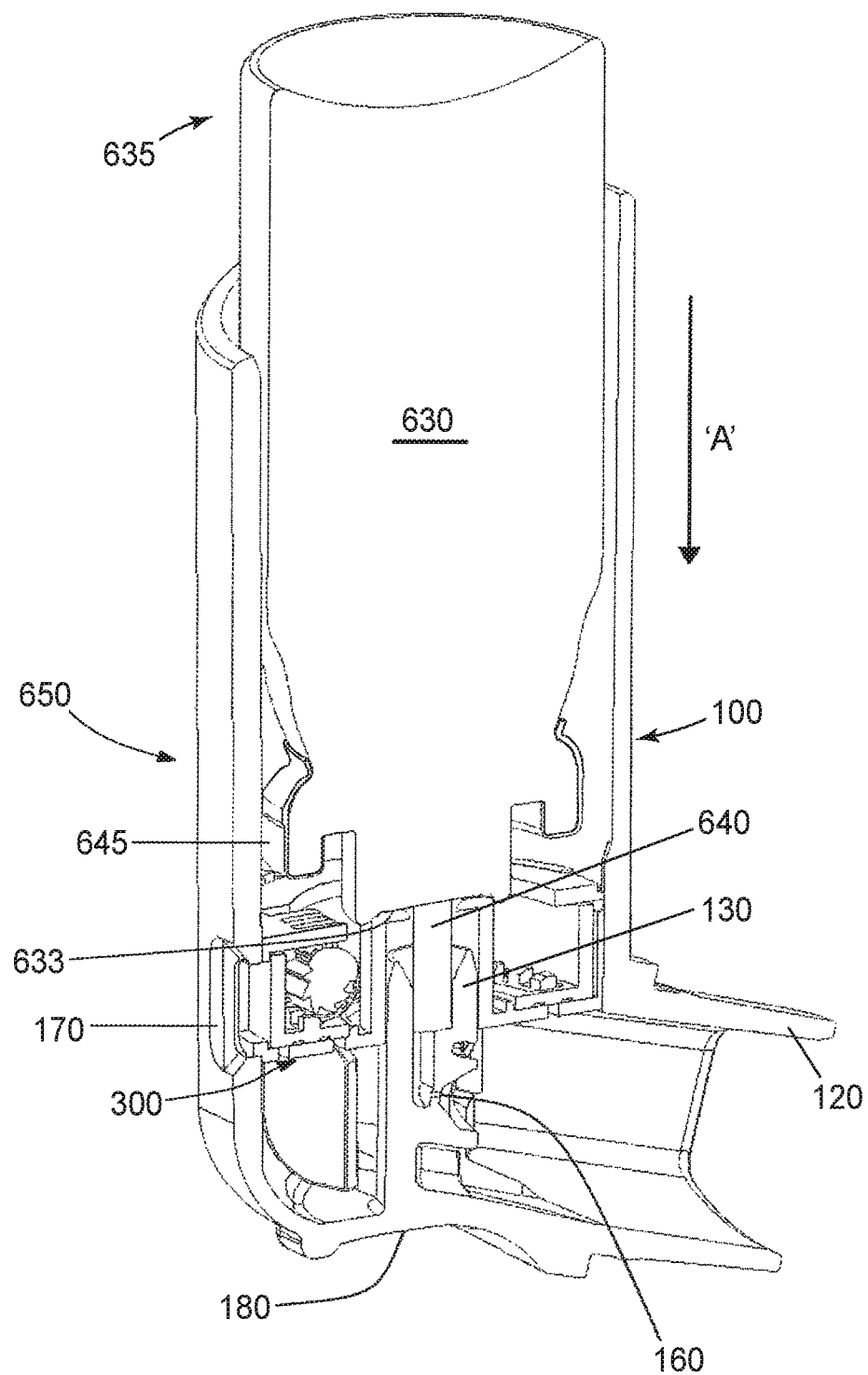
FIG. 14 illustrates a sectioned isometric view of a pMDI inhaler having a dose indicator in accordance with the first exemplary embodiment of the present invention.

After the dose indicator 300 has been located within the actuator 100, a conventional pMDI canister (FIG. 14) is inserted into the stem socket 140 of the nozzle block 130 through the aperture 500 of the indexing element 490 as shown in FIG. 14. A valve stem 640 associated with a metering valve on the container 630 is engaged with the nozzle block 130. Movement of the valve stem 640 towards the body of the container 630 opens the valve to dispense a metered amount of medicament. The combination of the pMDI container 630 and its associated metering valve together with the dose indicator 300 and actuator 100 is referred to hereinafter as the pMDI inhaler 650.

Downward pressure on the container 630, in the direction of arrow 'A', causes the valve stem 640 to open the associated valve allowing a metered amount of medicament to pass through the exit orifice 160 and into the mouthpiece 120 (see also FIG. 2). It is this downward pressure and opening of the valve to dispense a metered amount of medicament that needs to be indicated by the dose indicator 300 in accordance with the present invention.

When the user requires a dose of medicament, he/she takes his/her pMDI inhaler 650 and places the mouthpiece 120 within his/her mouth. To release a dose of medicament, the user then presses down upon the free end 635 of the container 630 (FIG. 14), whilst at the same time pressing upwards against the thumb grip 180, thereby causing the container 630 to move downwardly with respect to the valve stem 640. This movement discharges the aerosolised dose via the exit orifice 160 and mouthpiece 120 into the mouth and lungs of the user. The user then releases the downward force applied to the top 635 of the container 630, allowing it to return upwards relative to the valve stem 640 under the influence of an internal compression spring (not shown) associated with the valve.

Figure 15:
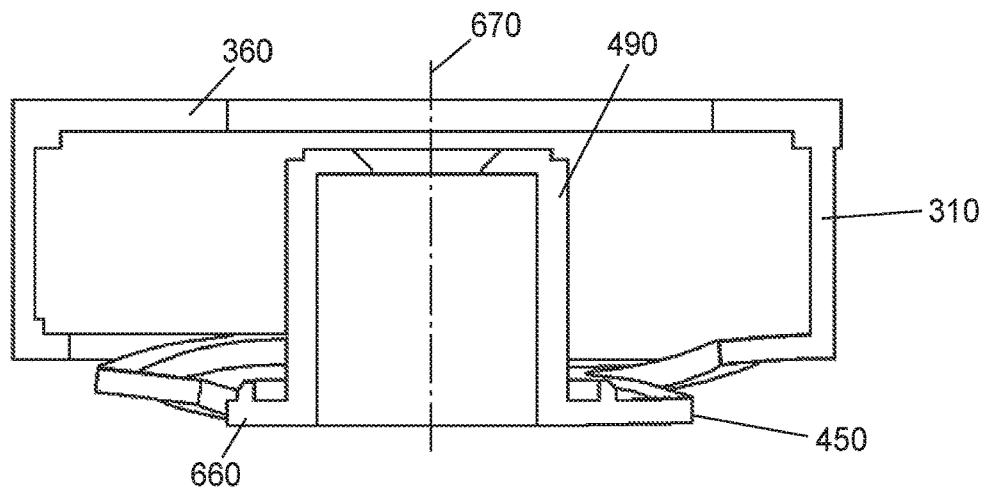
FIG. 15 illustrates a sectioned side view of a chassis element in accordance with the first exemplary embodiment of the present invention in its second or displaced position.

The dose indicator 300 registers the released dose as follows. As the container 630 moves downwards during user actuation, the lower surface 633 of a ferrule 645 of the valve pushes down against the top of the indexing element 490, causing it to move downwards relative to the outer wall 340, lid 360, display element 320 and worm element 330 of the dose indicator 300. This movement is made possible by the transient downwards displacement of an inner part 660 of the deformable grille element 450 as the grille element 450 elastically deforms. This is best shown in FIGS. 15 to 17.

Figure 16:
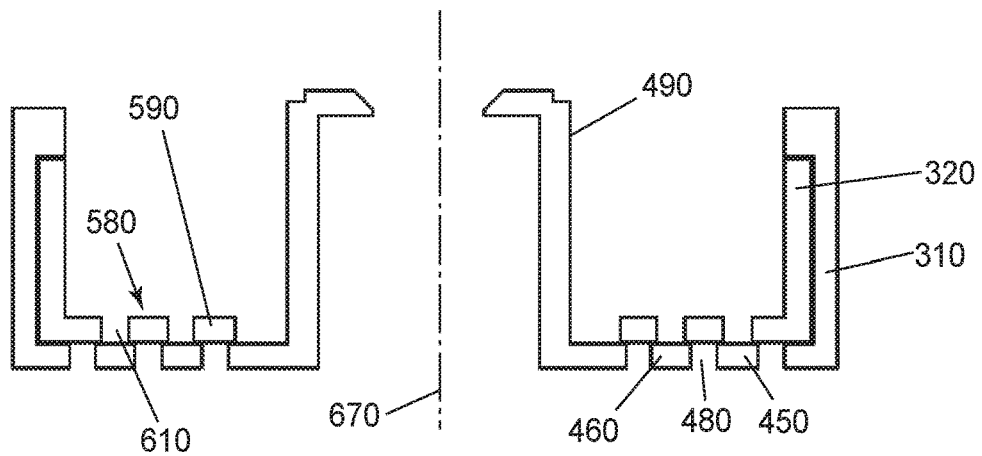
FIG. 16 illustrates a cross-section of a dose indicator in accordance with the first exemplary embodiment of the present invention with the indexing element in its first or rest position.
Figure 17:
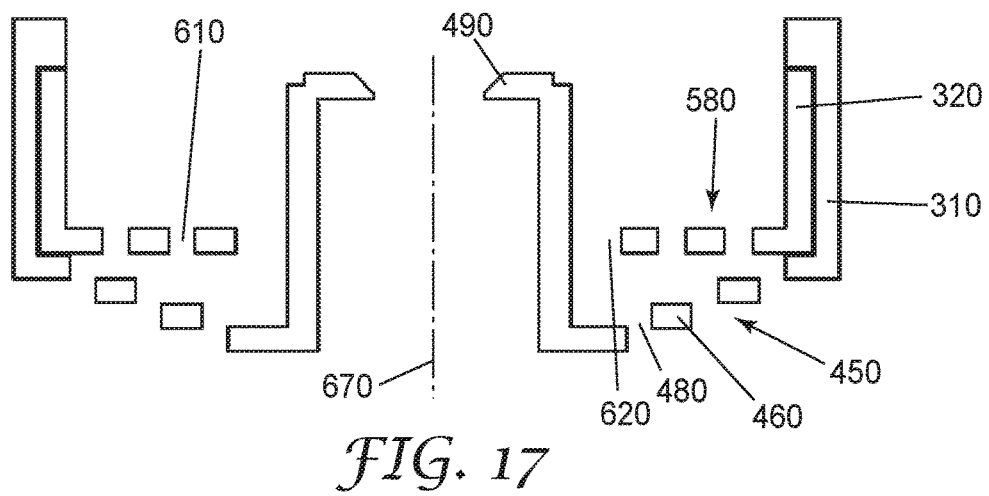
FIG. 17 is similar to FIG. 16 but illustrates the indexing element in its second or displaced position.
Figure 18:
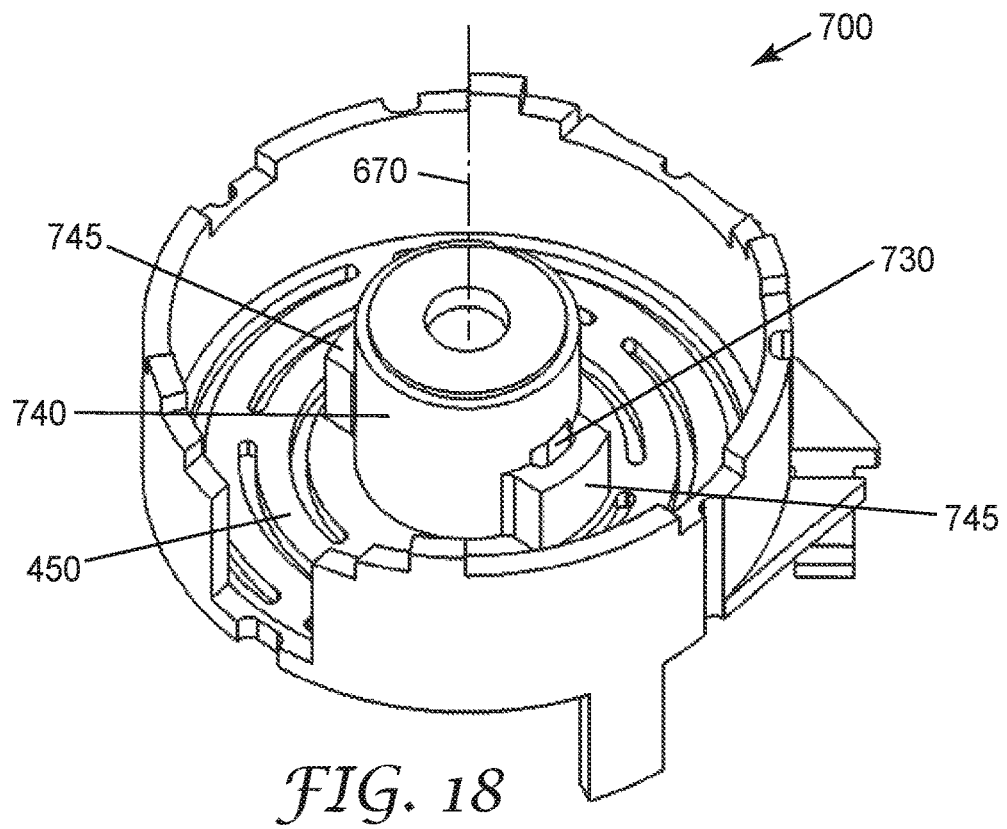
FIG. 18 illustrates a partial isometric top view of a chassis element in accordance with a second exemplary embodiment of the present invention, the lid not being shown for clarity.
Figure 19:
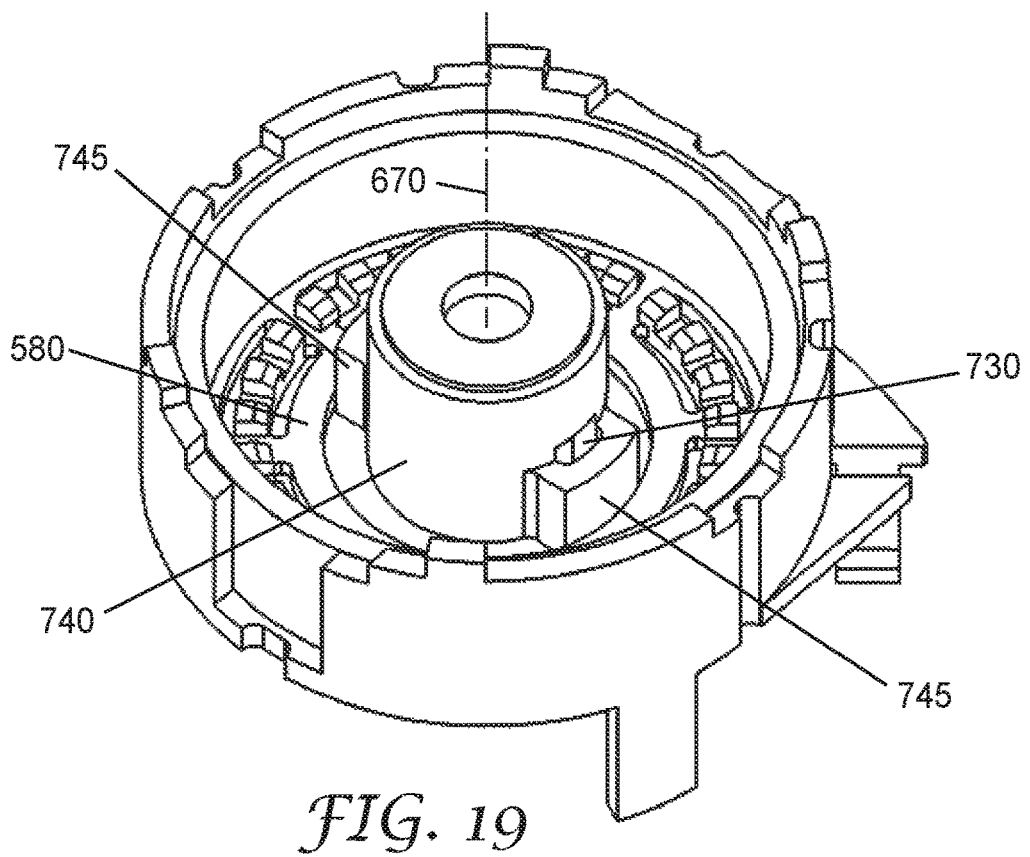
FIG. 19 is similar to FIG. 18 but also illustrates the display ring within the chassis element.
Figure 20:
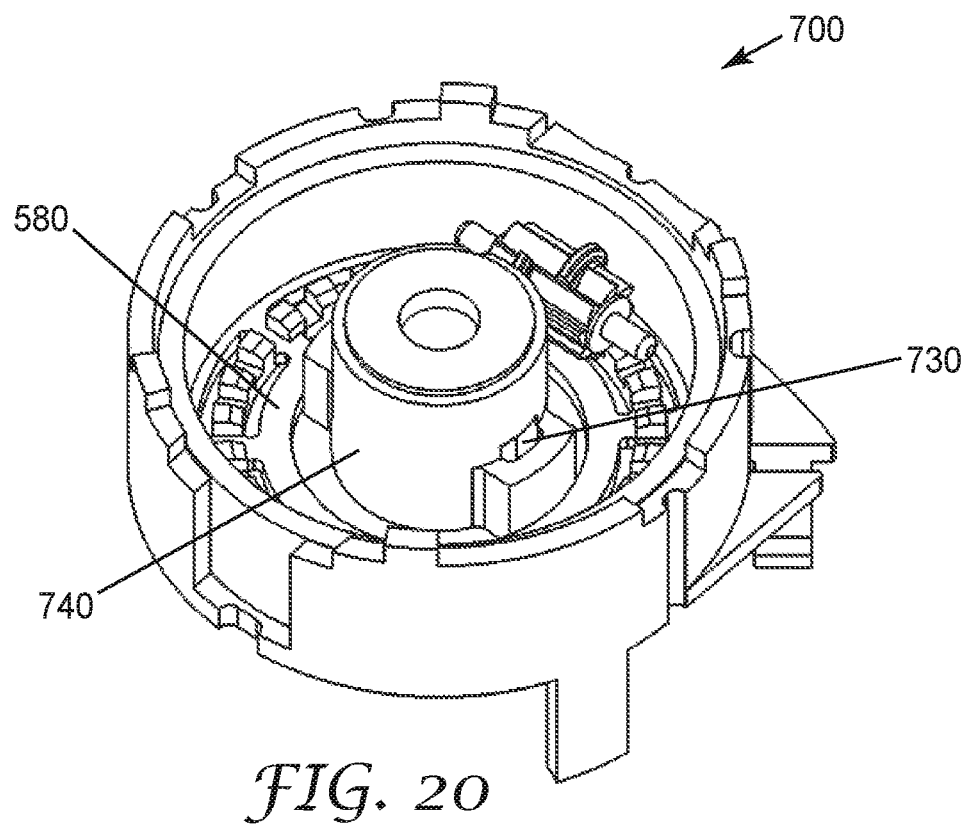
FIG. 20 is similar to FIG. 19 but also illustrates the worm element.

FIG. 16 shows the situation where the dose indicator 300 is in its rest position, with the deformable grille element 450 in a non-deformed state and the indexing element 490 in an upward or first position. FIGS. 15 and 17 show the indexing element 490 pushed downwardly, away from the lid 360, the deformable grille element 450 having become transiently deformed as a consequence of this downward movement.

Turning now to FIG. 12, as described above the advancement arm 510 is mounted on the inner part 660 of the deformable grille element 450, and thus it will move downwardly with the indexing element 490 as it is pushed down. As the advancement arm 510 is pushed downwards, a hook 515 at its upper end engages with one of the drive teeth 550 on the worm element 330, causing the worm element 330 to rotate clockwise as shown in FIG. 12. As there are eight teeth in this embodiment of the worm element 330, the clockwise rotation is approximately 45°. Any excess "follow through" motion of the container 630 and indexing element 490, for example, as a result of dimensional tolerances/ variation, will not affect operation of the dose indicator 300 as the advancement arm 510 is free to continue downwards once it has rotated and disengaged the teeth 550 of the worm element 330. The rotational movement of the worm element 330, in turn, rotates the display element 320 as the worm flight 560 engages with and drives the teeth of the rack 625 on the display element 320, the spacing of the teeth of the rack 625 corresponding to the flight of the worm element 330. The amount of rotation of the display element 320 will not be great, however, due to the gearing provided by the use of such a worm and rack arrangement. Nevertheless, the numerals (not shown) displayed via the window 170 of the actuator 100 and viewing portion 520 of the chassis element 310 to the user will move slightly, and, after multiple successive doses, the displayed numerals will change, for example, from "200" to "190", indicating a reduction of ten in the remaining number of medicament doses available to the user.

The gearing also serves to ensure that the display element 320 cannot readily be inappropriately rotated without discharging a dose, either forwards or backwards, by user intervention, for example, by inserting something through the window 170 of the actuator 100 and viewing portion 520 formed in the outer wall 340.

Completing the actuation cycle, the resilient deformable grille element 450, having deflected elastically, will act as a spring when it is released, serving to return the indexing element 490 back up to its rest or first position when the user stops pressing on the container 630 of the pMDI canister. The deformable grille element 450 will therefore return from the position illustrated in FIG. 17 to that illustrated in FIG. 16 once the pressure is released. The advancement arm 510 accordingly also returns to its own corresponding rest position. The worm element 330 cannot, however, rotate back to its previous position, as the locking pawl 440 (FIG. 11) engages with its teeth 550 and prevents any rotation. The hook 515 at the end of the advancement arm 510, meanwhile, returns past the worm teeth 550 by deflecting past them back to its first or rest position as shown in FIG. 12.

At the end of life, that is, for a displayed count of '0', an end-of-life stop feature (not shown) provides a restraint on further dose indicator display rotation. This feature could take several forms, such as missing teeth, filled in teeth, a raised boss or other feature, etc. in the display ring.

As will be seen from FIG. 16, in its rest position, the rings 460 of the deformable grille element 450 abut and occlude the slots 610 between the rings 590 of the grille element 580 of the display element 320, thereby providing a significant resistance to the inhalation of air through the slots of the grille elements 450, 580 by a user. By ensuring that the outer contours of the chassis element 310 match the inner contours of the actuator 100, bypass air leaks round the outside of the dose indicator can be minimised. When the container 630 is pushed downwardly, causing the indexing element 490 of the dose indicator 300 to be displaced downwardly as shown in FIG. 17, the rings 460 of the deformable grille element 450 move away from the slots 610 between the rings 590 of the grille element 580 of the display element 320, thereby significantly reducing the resistance to airflow. The sudden reduction of resistance effectively allows inhalation to start. By this means, the grille elements 450, 580 are able to provide a substantial measure of breath-coordination to the user.

By sucking on the mouthpiece 120 before depressing the container 630, the user is able to ensure that an inhaled airflow starts as the grille elements 450, 580 move apart. Advantageously the pMDI valve releases a dose of medicament while the grille elements 450, 580 are moving apart, preferably very soon after the inhaled airflow starts. This coordination of timing essentially ensures that the emitted aerosol of medicament particles is inhaled early in the respiratory manoeuvre of the user and thus reaches the deeper parts of the lungs where the medicament is most effective. As a result, the dose indicator 300 described above also provides a breath-coordination system for a user.

In alternative embodiments (not shown), the rings of the deformable grille element 450 may be configured never to occlude the slots 610 of the other grille element 580, and/or bypass air channels can be provided between the chassis element 310 and the actuator 100, for example in conjunction with a continuous, non-perforated deformable grille element 450. Such alternative embodiments serve to provide low cost dose indication with minimal changes to the inhaler actuator and a low component count, without breath coordination.

In a preferred embodiment, the indexing element 490 has a central axis 670 passing through the centre of the central aperture 500 and extending in a direction that is substantially perpendicular to the plane of the deformable grille element 450 as shown in FIGS. 6, 10 to 12 and 15 to 17. The central axis 670 also provides an alignment reference for the display element 320 within the chassis element 310, for the deformation of the resilient deformable grille element 450 in the same direction as the translation of the indexing element 490 from a first position (FIGS. 11, 12 and 16) to a second position (FIGS. 15 and 17), and for the location of the dose indicator 300 on the stem socket 140 of the nozzle block 130 (FIG. 1).

As shown in FIGS. 15 and 17, the deformation of the resilient deformable grille element 450 forms an inverted frustrum of a cone which is centred about the axis 670.

FIGS. 18 to 22 show a second exemplary embodiment of a dose indicator 700 in accordance with the present invention. In general, this exemplary embodiment is similar to the exemplary embodiment described above with reference to FIGS. 4 to 17 but differs from it in one principal way. In order to provide a greater return spring force than is provided by the deformable grille element 450 alone, the second embodiment has two additional spring arms. In particular, these spring arms are arranged to provide a restorative spring force even when the dose indicator is in its rest position, something which the deformable grille element 450 does not provide.

It will be appreciated that the resilient deformable grille element 450 of either the first or the second embodiment could be configured to provide a restorative spring force when the dose indicator is in its rest position. However, in such a configuration, it is difficult to ensure that adequate resistance to air is provided in the rest position. This is due to having to mould the resilient deformable grille element 450 in a non-planar form which becomes accurately and reliably planar in the rest position of the dose indicator 300, 700. The deformable grille element 450 needs to be substantially planar when the dose indicator is at rest, in order to provide acceptably high initial resistance to inhaled airflow through the system.

Components that are the same in both the first and second exemplary embodiments of the dose indicator 300, 700 are referenced the same.

Figure 21:
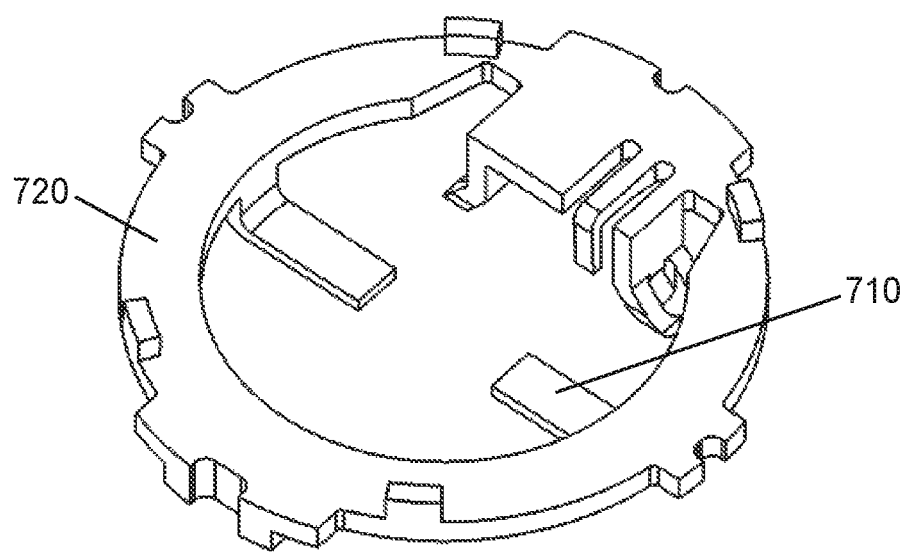
FIG. 21 illustrates an isometric top view of the lid part only of the chassis element in accordance with the second exemplary embodiment of the present invention.

FIG. 21 best shows the additional spring arms 710 (although they are also visible in FIG. 22), which are formed integrally with lid 720. These arms 710 are configured so that their tips fit into holes 730 provided in the sides of the indexing element 740. The lower part of the indexing element 740 has wings 745 protruding from diametrically opposite regions. These allow through holes 730 to be formed in the side wall of the indexing element 730 during injection moulding, without the need for side-action tooling.

Figure 22:
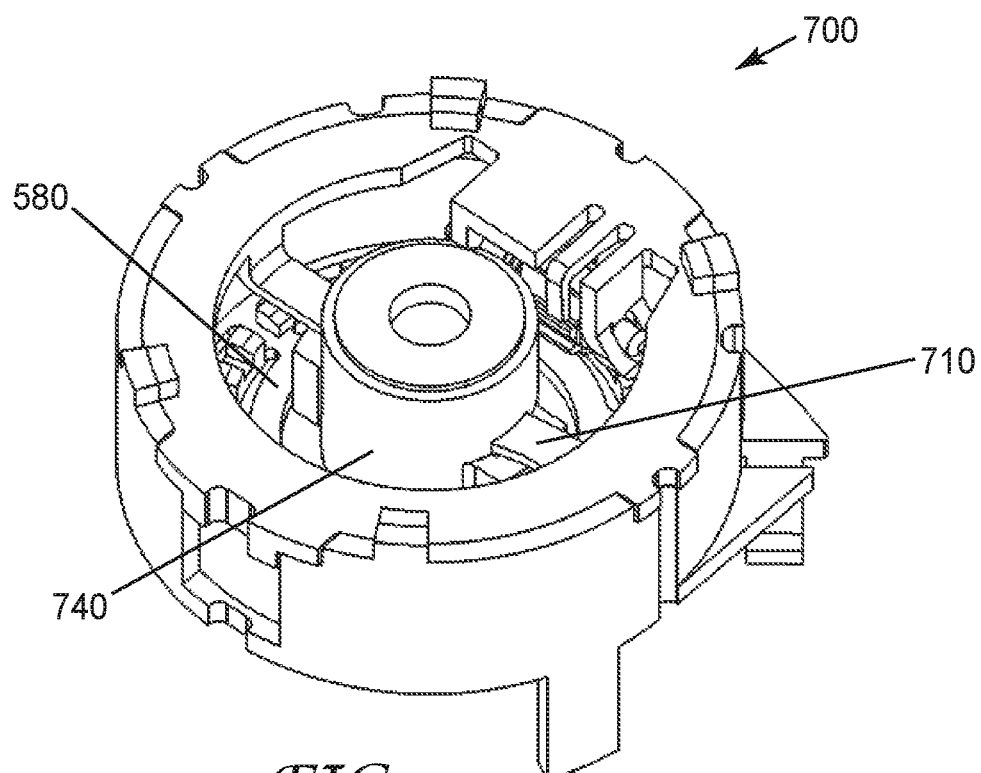
FIG. 22 illustrates an isometric top view of the assembled dose indicator in accordance with the second exemplary embodiment of the present invention.
Figure 23:
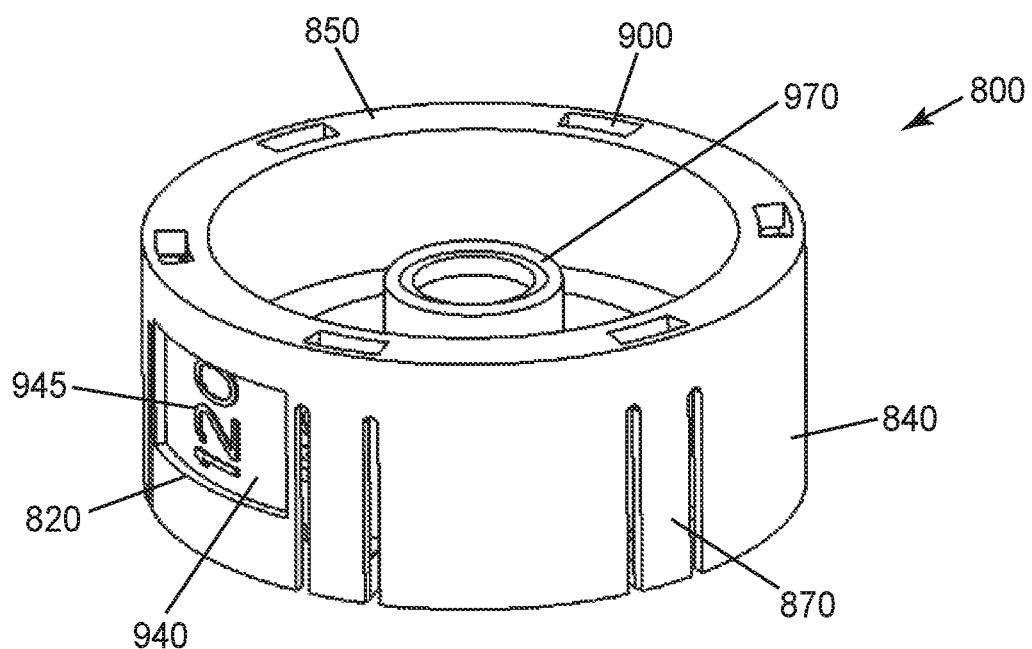
FIG. 23 illustrates an isometric top view of a dose indicator in accordance with a third exemplary embodiment of the present invention.

FIG. 22 shows the assembled dose indicator 700 of the second exemplary embodiment, showing that the tips (not shown) of the additional spring arms 710 are pushed into the holes 730. Although not readily evident from this Figure, the two spring arms 710 are downwardly elastically deflected with generally greater downward deflection towards their tips in this rest position of the dose indicator 700. This deflection causes a resultant upward force to be applied by the spring arms 710 to the indexing element 740, thereby providing a restorative upward force to the deformable grille element 450, even in its rest position.

In FIGS. 18 to 22, the indexing element 740 of the dose indicator 700 also has a central axis 670 passing through the centre of the central aperture 500 and extending in a direction that is substantially perpendicular to the plane of the deformable grille element 450. This central axis provides an alignment reference for the display element 320 within the chassis element 310, for the deformation of the resilient deformable grille element 450 as it is deformed by translation of the indexing element 740 from a first position to a second position, and for the location of the dose indicator 300 on the stem socket 140 of the nozzle block 130 as described above with reference to the first exemplary embodiment of the dose indicator 300 (see FIG. 2).

In summary, the first and second exemplary embodiments in accordance with the present invention each provide a simple dose indicator with a ten-dose resolution that counts down inhaler actuations from 200 to zero. Their design is space-efficient and is compatible with inhalers of familiar shape and size to users, and they each require only three additional components compared to a standard pMDI inhaler, thereby meeting the market need for sufficiently low cost. In addition, as shown by the illustrated exemplary embodiments, the design can also, advantageously, incorporate a built-in integrated breath coordination system of the "can't breathe until press" type. In addition to these advantages and benefits, the dose indicator can clip together as a robust sub-assembly/module, reducing dimensional tolerance issues. The dose indicator may preferably be designed to provide count-before-fire reassurance, in order to minimise the possibility of under-counting. If the user fails to 'follow through' to valve actuation after indexing the dose indicator, the dose indicator will indicate fewer doses remain than is actually the case. This is deemed to be safer than the alternative where the user might actuate the valve to dispense a dose but might then fail to follow through to register the count, that is, to index the dose indicator. In that case, the dose indicator might register more remaining doses than is actually the case, leading to a potentially dangerous situation where the user is led to believe they have more doses left than there are in reality. Note that manufacturing tolerances mean that it is never possible to guarantee that valve actuation and dose indicator advancement occur exactly simultaneously in any mechanical system: the choice has to be made which is designed to occur first.

The three elements of the dose indicator can be cheaply moulded, for example, injection moulded, from "non-engineering grade" polymer, such as a polyolefin such as polyethylene or polypropylene. Polypropylene is preferred as it allows the creation of the living hinge as described above.

Turning now to a third exemplary embodiment of a dose indicator 800 in accordance with the present invention, reference is made to FIGS. 23 to 32. The dose indicator 800 is similar to the exemplary dose indicators 300 described above in that it has a chassis element 810 with a viewing portion 820 through which a portion of a display element 830 can be seen. However, in this embodiment, the chassis element 810 and the display element 830 are the only two components.

Figure 25:
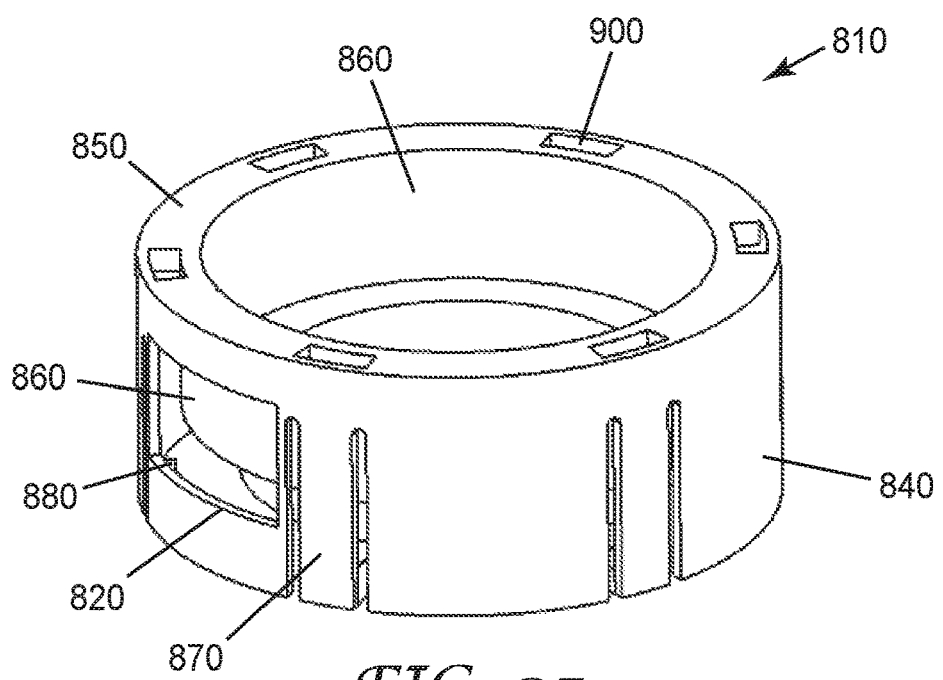
FIG. 25 illustrates an isometric top view of a chassis element in accordance with the third exemplary embodiment of the present invention.
Figure 26:
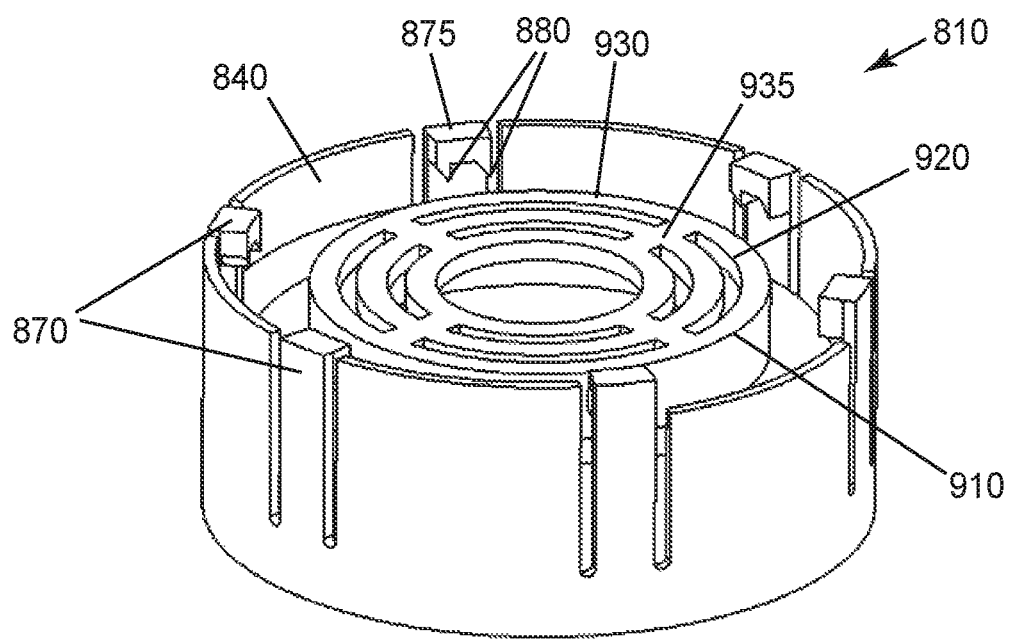
FIG. 26 illustrates an isometric bottom view of a chassis element in accordance with the third exemplary embodiment of the present invention.

With reference to FIGS. 25 and 26 in particular, the chassis element 810 comprises a generally rigid outer wall 840, joined via an upper rim 850 to an inner wall 860. At multiple, in this embodiment six, locations around the outer wall 840 flexible clips 870 are formed which serve to retain the display element 830 when assembled. The bottom ends 875 of these clips 870 each bear two teeth 880. Similar teeth 890, but mounted facing down rather than up, are provided in pairs on the underside of the upper rim 850, as may be seen in FIGS. 30 and 31. Apertures 900 serve to allow injection moulding of the clips 870. As described above, a viewing portion 820 is provided in the outer wall 840 which aligns with the window 170 (FIG. 1) to enable viewing of the displayed count. As shown in FIG. 26, the chassis element 810 also includes a grille element 910 having grille slots 920 formed by rings 930 joined by radial members 935 in a similar way to the grille element 580 of the display element 320.

Figure 27:
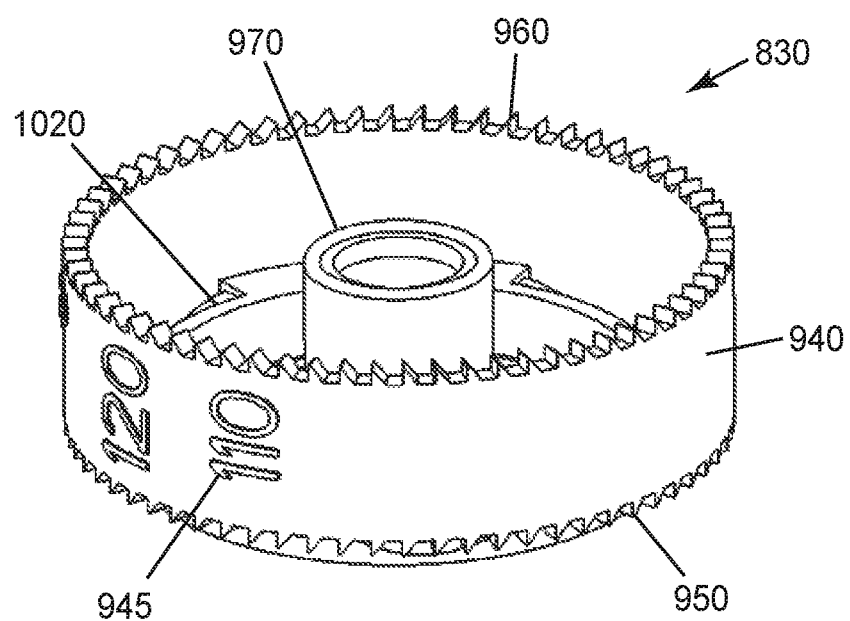
FIG. 27 illustrates an isometric top view of a display element in accordance with the third exemplary embodiment of the present invention (not all display numerals being shown)
Figure 28:
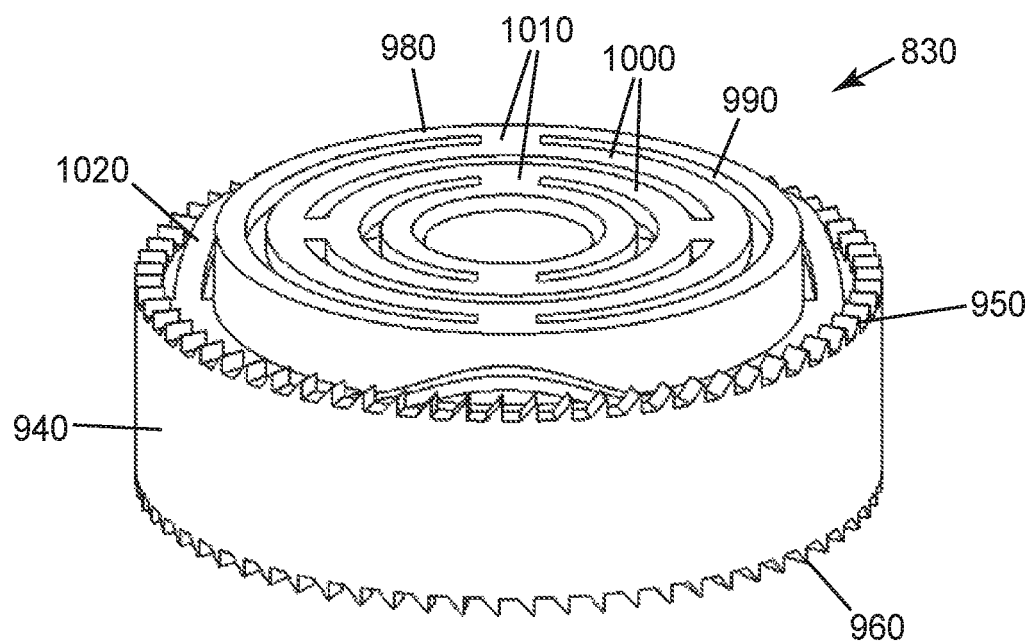
FIG. 28 illustrates an isometric bottom view of the display element of FIG. 27 (display numerals not being shown)
Figure 29:
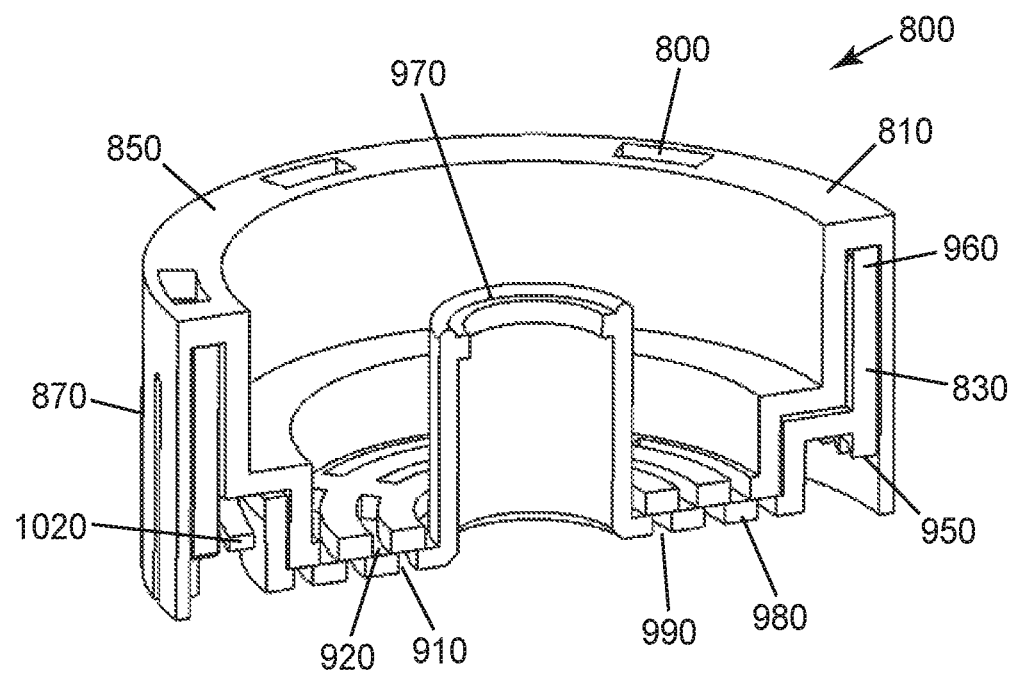
FIG. 29 illustrates a sectioned isometric top view of the dose indicator in accordance with the third exemplary embodiment of the present invention in its first or rest position.

With reference to FIGS. 27 and 28 in particular, the display element 830 comprises a rigid display ring 940, on the outer surface of which are provided numerals 945 (not all shown in FIG. 27) corresponding to hundreds, tens and units digits of dose counts. For example, there may be thirteen sets of these numerals, from '120' down to '0' in counts of ten (not all shown in the relevant Figures), arranged anticlockwise as viewed from the top of the display element 830. At the bottom of the display ring 940 is provided a set of lower teeth 950 and at the top thereof is provided a set of upper teeth 960.

Figure 30:
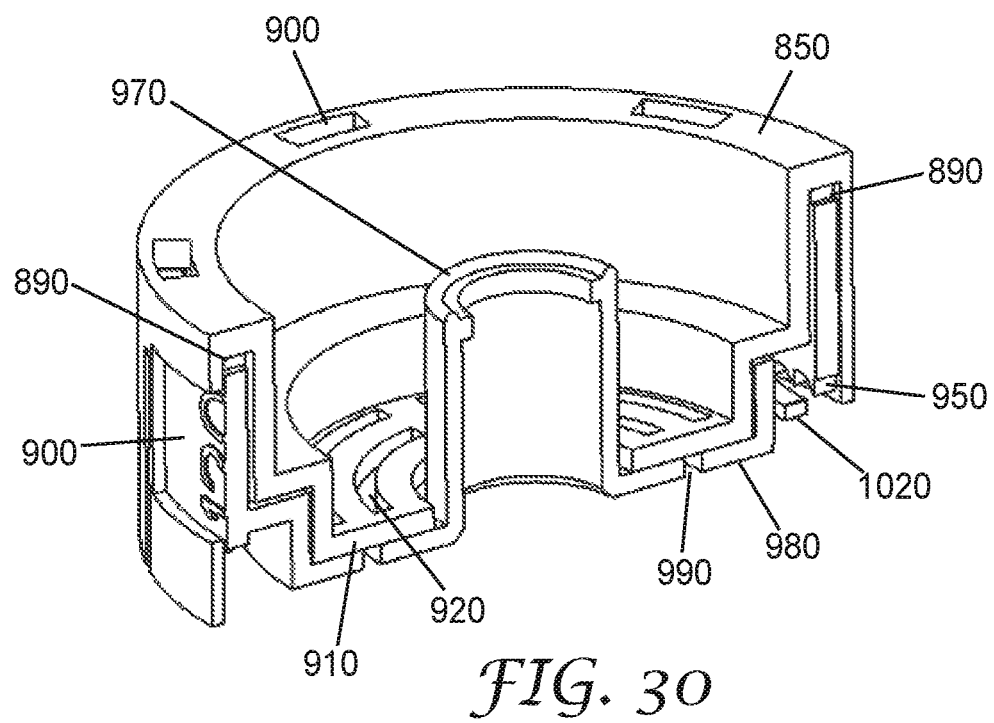
FIG. 30 is similar to FIG. 29 but illustrates the display ring and viewing window.
Figure 31:
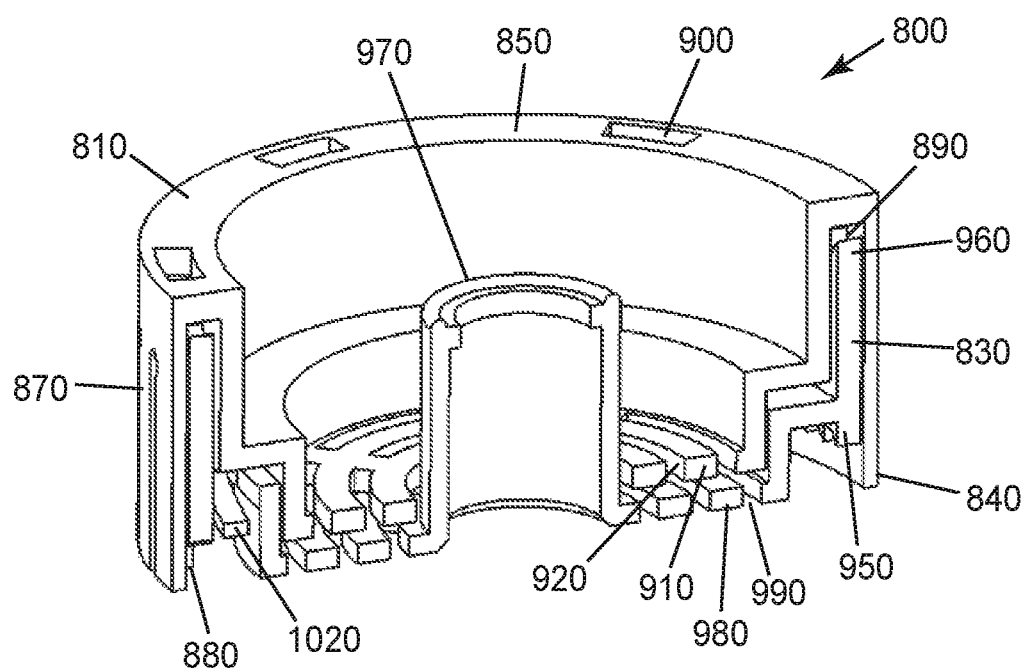
FIG. 31 is similar to FIG. 29 but illustrates the dose indicator in its second or displaced position.

The display ring portion 940 is connected to an indexing element or a central alignment tube 970, for example, as may be seen more clearly in FIGS. 30 and 31, via a flat labyrinthine follow-through spring 980 (FIG. 28). The follow-through spring 980 comprises spring slots 990 which are defined by rings 1000 joined by radial members 1010 as shown. This is similar to the deformable grille element 450 of the first exemplary embodiment of the dose indicator 300 described above with reference to FIGS. 4 to 17.

Protruding downwards from the inside of the display element 830 are three counter spring arms 1020 in the form of three bows, each spring arm 1020 being joined at both ends rather than cantilevered (FIG. 28). These spring arms 1020 press against the actuator running surface 190 (FIG. 1) and bias the upper sets of teeth 890, 960 into mutual engagement while separating the lower sets of teeth 880, 950 from one another. When the container is pushed downwards by a user, as described above, to release a dose of medicament formulation, the spring arms 1020 flatten out against the running surface 190, they provide a resistive force that serves to separate the lower sets of teeth 880, 950 from one another and to bring the upper sets of teeth 890, 960 into mutual engagement to complete a complete unit decrement of the system, when the user subsequently removes their downward pressure on the pMDI canister (not shown) as described above.

For a typically sized pMDI inhaler, the outside diameter of the display ring 940, and hence the display element 830, is approximately 23 mm. For a 120-count display indicator, 132 teeth may typically be provided so as to allow for a few factory advancements/counts during assembly, plus an end-of-count stop feature location, etc. For a 23 mm diameter ring and 132 teeth, each tooth would occupy 360°/132, that is approximately 2.7°, of the circumference, or approximately 0.55 mm. Such teeth are large enough to be reliably injection moulded. As shown in FIG. 28, the same number of teeth are provided in the upper set of teeth 960 and the lower set of teeth 950 but the upper set is offset with respect to the lower set.

Figure 24:
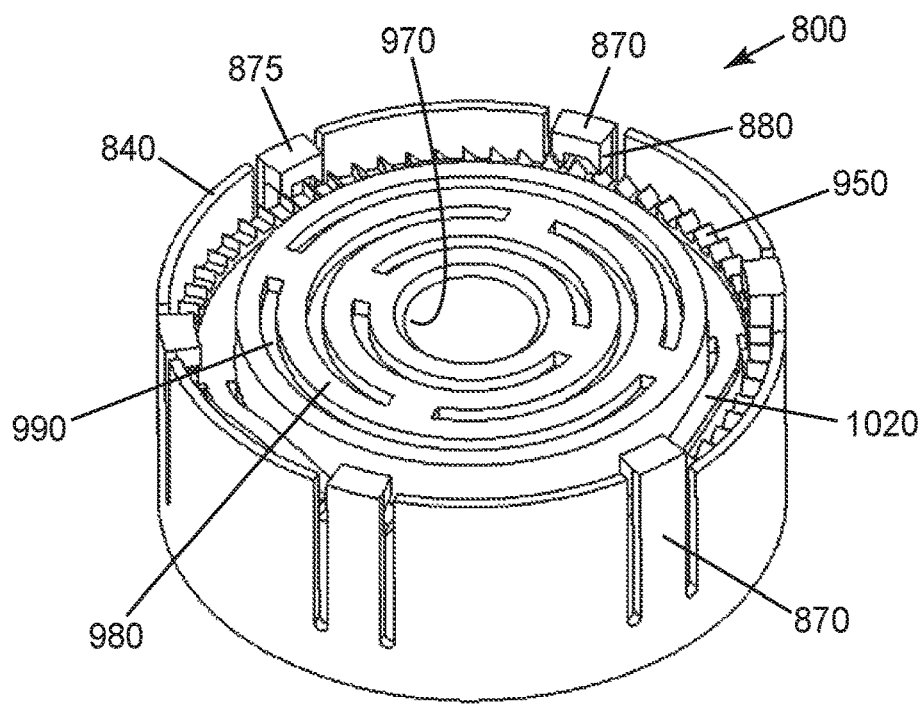
FIG. 24 illustrates an isometric bottom view of a dose indicator in accordance with the third exemplary embodiment of the present invention.

It is, however, preferable not to provide all 132 teeth. Instead, as shown in FIGS. 24, 27 and 28, only alternate teeth are provided in both the upper and lower sets of teeth on the display ring 940. This has the advantages of being easier to mould (the moulding tooling does not need such fine metal features), and also of avoiding the small dirt traps between teeth that a full set of 132 teeth would create. By having alternate teeth that are offset between the upper set and the lower set, lower frictional forces tend to be experienced.

As can be seen in FIGS. 24 and 26, the teeth 880 on the chassis element 810 are also not immediate neighbours. In this case, two consecutive teeth are "missing", meaning that the pairs of teeth provided, that is, the bottom teeth 880 on the chassis clips 870, each comprise teeth that are three positions apart. Because these are an odd number of teeth positions apart, then one of the pair will always be engaged with one of the teeth of the display element 830. In other words, the display element 830 and the display ring 940 will be rotated by a single increment of approximately 2.7° for each dose taken, even though not all the 132 nominal teeth are present in any of the sets of teeth. Hereafter, where a pitch of one tooth is referred to, it will be understood to correspond to a single increment of the display ring despite any missing teeth.

As described above with reference to the first exemplary embodiment, the indexing element 970 has an axis (not shown) about which the display ring 830 and the chassis element 810 are arranged.

The arrangement of the assembled components is as follows. The display element 830 sits in the annular gap between the inner wall 860 and the outer wall 840 of the chassis element 81, and is held loosely captive by the bottom ends of the clips 870 of the chassis element 810. The chassis element 810 is, in turn, retained in place near the bottom of the actuator 100 so that it is correctly rotationally aligned and it is prevented from rotational movement relative to the actuator 100. Appropriate clipping features (not shown) may be provided, for example, undercut clipping features can be moulded into the actuator 100 via moulding tool side-core actions at the mouthpiece 120 and window 170. The pMDI canister (not shown) is a simple push-fit into the actuator 100, with a valve stem associated with the valve pushing into the stem socket 140 of the nozzle block 130. The ferrule of the valve (not shown) is arranged to sit adjacent to the upper end of the central alignment tube or indexing element 970 of the display element 830 in the assembled dose indicator 800.

In use, the user actuates the inhaler by pressing down on the pMDI canister (not shown), by squeezing their thumb and finger(s) together against the canister base and the thumb grip 180. This action tends to push the container of the pMDI canister down relative to the valve stem of the metering valve (not shown), which is restrained in the stem socket 140 of the actuator 100. As the user continues to press, the ferrule of the valve contacts the central alignment tube or indexing element 970 if the two were not already in contact. As the valve continues to move downwards, it causes the counter spring arms 1020 to flex, these being less stiff than the follow-through spring 980. As the counter spring arms 1020 flex, they allow the lower teeth 950 of the display ring 940 to engage with the lower teeth 880 of the chassis element 810, the full engagement of which causes the display element 830 and display ring 940 to rotate by approximately half the pitch of the teeth in a clockwise direction as viewed from above.

Figure 32:
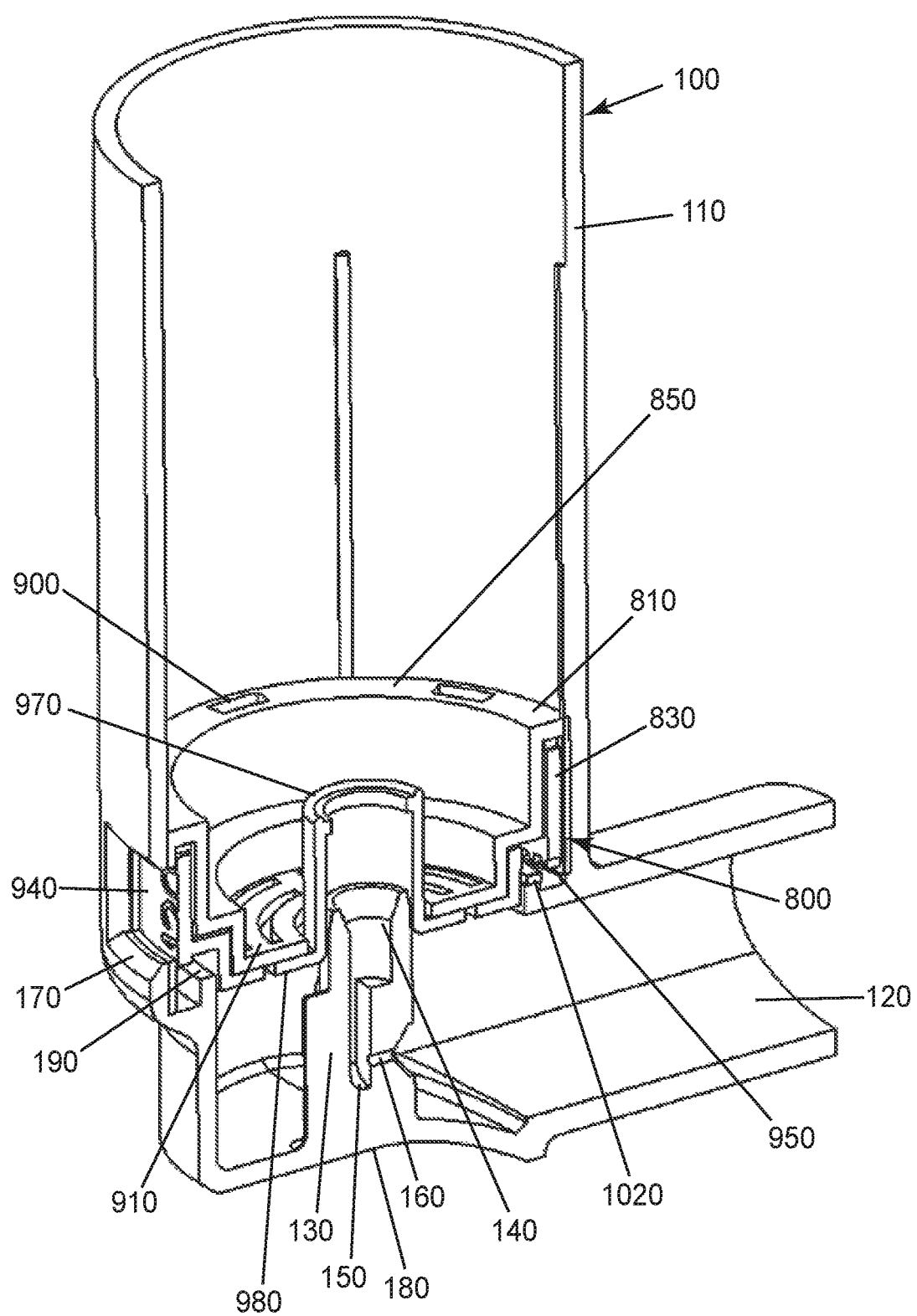
FIG. 32 illustrates a sectioned isometric top view of the assembled dose indicator in accordance with the third exemplary embodiment of the present invention mounted within a pMDI actuator.

With the teeth now fully engaged, further user depression of the container of the pMDI canister towards the thumb grip 180 does not result in any further motion of the display element 830, either axially or rotationally, as the engaged lower teeth 880, 950 will not allow it. The follow-through spring 980, however, is able to flex (as will be described later) to allow further 'follow-through' motion of the container of the pMDI canister relative to the stem socket 140. The valve stem (not shown) thus moves further inwardly relative to the rest of the metering valve, and this (in ways familiar to those skilled in the art) causes the valve to dispense a metered dose of medicament formulation out via the bore of the valve stem, into the sump 150, through the exit orifice 160, and into the mouthpiece 120, as shown in FIG. 32, for inhalation by the user.

In this manner, with the counter spring arms 1020 being less rigid than the follow-through spring 980, 'count before fire' is assured, that is, the display element 830 increments before the valve dispenses a dose. Therefore, if the user fails to 'follow through' to valve actuation after the display element 830 and display ring 940 has been incremented, the dose indicator will indicate that fewer doses remain than is actually the case. This is deemed to be safer than the alternative where the user might actuate the valve to dispense a dose but might then fail to follow through to register the count, that is, to increment the dose indicator, as described above.

After receiving the dose, the user then relaxes their grip on the pMDI canister (not shown) and thumb grip 180. This allows the follow-through spring 980 to start to relax, which in turn allows the weaker counter spring arms 1020 to relax. As the springs relax, the counter spring arms 1020 push the set of lower teeth 950 on the display ring 940 out of engagement with the lower teeth 880 of the chassis element 810 and then push the upper set of teeth 960 into engagement with the upper teeth 890 of the chassis element 810. The full engagement of the upper teeth 890, 960 causes the display element 830 and display ring 940 to rotate by a further approximately half tooth pitch in a clockwise direction as viewed from above. When the user completely releases the system, it has been returned to its starting point except that a dose has been released and the display element 830 and display ring 940 of the dose indicator 810 has now been rotated by the pitch of one tooth in a clockwise direction as viewed from above. A spring (not shown) inside the pMDI metering valve resets the valve, in a manner that will be apparent to one skilled in the art. The numerals 945 displayed in the window 170 of the actuator 100 have thus moved in a downwards-counting direction, for example, from a displayed count of '120' in the direction of '110'.

After this process has been repeated ten times, that is, ten consecutive doses have been dispensed, the displayed numerals will have moved by ten times the pitch of the teeth, corresponding to the distance between sets of numerals 945 on the display ring 940 of the display element 830. For example, the displayed count might have moved from '120' to '110'. As described above, the window 170 is large enough for the user to see up to two sets of numerals, e.g. '120' and '110', so that both are visible when the actual count corresponds to an intermediate number, e.g. '116' or '115'. In this manner, the user can observe the shifted position of the display ring 940 and can appreciate that the count has gone from, for example, a hundred and sixteen doses remaining to a hundred and fifteen doses remaining.

Although the display element 830, and hence the display ring 940, has been described as being indexed a half pitch on translation of the indexing element from the first position to the second position and a half pitch on the return from the second position to the first position, it will be appreciated that any suitable fraction of the pitch between the teeth can be implemented during the movement from the first position to the second position with the remaining fraction of the pitch being implemented on the return from the second position to the first position.

At the end of life, that is, a displayed count of '0', an end-of-life stop feature (not shown) would provide a restraint on further dose indicator display rotation. This feature could take several forms, for example, missing teeth, filled in teeth, a raised boss or other feature, etc.

The third exemplary embodiment in accordance with the present invention provides a simple dose indicator 800 with a ten-dose resolution that counts down inhaler actuations from 120 to zero. The exemplary embodiment provides a dose indicator that can be implemented in a desirably space-efficient manner, allowing for compatibility with pMDI inhalers of familiar shape and size to users, and in particular its design only requires two additional components, thereby meeting the market need for sufficiently low cost. In addition, this exemplary dose indicator also, advantageously, incorporates a built-in integrated breath coordination system of the "can't breathe until press" type. As described above, the labyrinthine follow-through spring 980 comprises a series of curved spring arms with curved slots 990 between them. When these slots 990 are unobstructed, inhaled air is able to pass through them as it makes its way down between the pMDI canister and the actuator 100 towards the mouthpiece 120 and the lungs (not shown) of a user.

When the exemplary dose indicator 800 is in its rest position, these slots 990 are adjacent to the curved bars 930 of the grille element 910 provided on the chassis element 810. In this position, the slots 990 are therefore obstructed, so that when the user tries to inhale through the mouthpiece 120, the resulting high resistance to airflow is uncomfortable and prevents significant respiratory air flow.

As the user presses down on the base of the pMDI canister in order to deliver a dose, as described above, the central alignment tube or indexing element 970 is pushed down by the pMDI valve (not shown). At first, the display element 830 will tend to translate downwards, for example, from the position shown in FIG. 29 to that shown in FIG. 31. As will be noted, this movement causes the curved arms of the follow-through spring 980 to move away from the slots 920 between the bars 930, 935 of the grille element 910, and the slots 990 in the follow-through spring 980 to move away from the bars of the grille element 910. In this way, an airflow path of low resistance is opened up through the two sets of slots 920, 990. Further downward movement of the pMDI valve, and hence of the central alignment tube or indexing element 970, will increasingly cause the centre of the follow-through spring 980 to move down further than its edges, the latter being impeded by engagement of the lower set of teeth 950 of the display ring 940 with the lower set of teeth 880 of the chassis element 810 and by the increasing resistive force from the three counter spring arms 1020 as they flatten out. As the centre of the follow-through spring 980 moves further, to allow actuation of the pMDI valve, the follow-through spring 980 will thus tend to adopt a conical shape (not shown).

The third exemplary embodiment described herein provides, amongst other features and benefits, a self-contained, integrated dose indicator and breath coordination system for a pMDI inhaler which needs only two extra components compared to a standard pMDI inhaler without a dose indicator or dose counter, and which allows the registering and display of the usage of 120 actuations or more. By using a split-count approach, with partial indicator advancement on the down-stroke, the count decrement being completed on the subsequent up-stroke, advancement of the display ring 940 with respect to the chassis element 810 is ensured.

It will be appreciated that other split-count approaches may also be implemented which do not require the upper and lower teeth on the display ring 940 and the upper and lower teeth on the chassis element 810. For example, indexing features may be provided on the inner wall 860 of the chassis element 810 and on the inside of the display ring 940, for example, the tab or groove arrangements described in U.S. Pat. No. 5,718,355 particularly at column 15, line 64 to column 17, line 19 and in FIGS. 3E to 3H.

Advantageously, all four sets of teeth are provided by only two components which clip together to form a robust module in which dimensional tolerance issues are substantially reduced. Additionally, the use of the follow-through spring as part of a breath coordination system provides transient flow channel obstruction without incurring cost by having to include additional components.

The dose indicator of the third exemplary embodiment is designed for count-before-fire reassurance to avoid undercounting of the remaining doses in the associated pMDI inhaler.

In alternative embodiments (not shown), the curved bars 930 of the grille element 910 may be configured never to occlude the slots 990 of the follow-through spring 980 and/or bypass air channels can be provided between the chassis element 810 and the actuator 100, for example, in conjunction with a continuous, non-perforated deformable grille element. Such alternative embodiments serve to provide low cost dose indication with minimal changes to the inhaler actuator and a low component count, without breath coordination.

In addition, there is no need for small teeth to be provided on the display ring which is of particular benefit where the display ring is to be moulded, for example, injection moulded, cheaply from "non-engineering grade" polymer, such as a polyolefin such as polyethylene or polypropylene.

Although the exemplary embodiments of dose indicators described herein that are integrated with breath coordination functionality utilise a breath coordination system of the "can't breathe until press" type, other types of breath coordination system, for example, a transient holding chamber for the fired dose, opened upon subsequent user inhalation, could alternatively be used.

It will be apparent to one skilled in the art that many modifications and variants can be envisaged, without departing from the scope of the present invention. For example, different total numbers of actuations could be indicated, for example, 100 or 50, rather than 120; and colour bands could be used instead of (or in addition to) numerical indications on the display ring.

Whilst designed to be compatible with most metering valve types, it will be appreciated that minor changes to the profiles and forms of the chassis element and the display element may be necessary to incorporate different valve types.

The dose indicator in accordance with the embodiments of the present invention can be provided as a sub-assembly for insertion into pMDI inhalers. Alternatively, they could be provided within a separate housing component, as a stand-alone unit, for example for top-mounting on the base of a container of a pMDI canister as an alternative to mounting within the actuator. However, it will be appreciated that in this case, modifications within the skilled person's normal technical skills, for example, modifications linked to mounting the dose indicator on the base of the container of the pMDI canister, may be needed to ensure that the display ring is correctly indexed.

It will be appreciated that, although the dose indicators of the present invention have been described for use with an actuator that enables a user to breathe in through his/her mouth, the present invention is also suitable for use in nasal actuators where the mouthpiece can be replaced by a nosepiece.

The invention claimed is:

1. A dose indicator for a pressure-actuated metered fluid dispensing device, the dose indicator comprising:
    a chassis element having a viewing portion;
    a display element located within the chassis element;
    a resilient deformable element; and
    an indexing element having an axis, translation of the indexing element along its axis from a first position to a second position causing deformation of the resilient deformable element in the same direction as translation of the indexing element resulting in generally greater displacement of portions of the resilient deformable element nearer to the axis relative to portions thereof further from the axis, the displacement of the portions of the resilient deformable element in the same direction as translation of the indexing element inducing indexing of the display element from a current position to a subsequent position relative to the viewing portion of the chassis element, wherein the outline shape of the resulting displacement of the resilient deformable element comprises an inverted frustum of a cone.

2. A dose indicator according to claim 1, wherein the resilient deformable element is arranged around the axis of the indexing element.

3. A dose indicator according to claim 1, wherein the outline shape of the resulting displacement of the resilient deformable element is symmetrical about the axis.

4. A dose indicator according to claim 1, wherein the display element is arranged around the axis of the indexing element.

5. A dose indicator according to claim 1, wherein the display element comprises a continuous display ring.

6. A dose indicator according to claim 1, wherein the display element comprises a discontinuous ring.

7. A dose indicator according to claim 1, wherein the display element comprises a disc centred about the axis of the indexing element.

8. A dose indicator according to claim 1, wherein the indexing element comprises a tube element connected to the resilient deformable element.

9. A dose indicator according to claim 1, wherein the resilient deformable element comprises a grille element.

10. A dose indicator according to claim 9, further comprising a further grille element located adjacent the resilient deformable grille element, the further grille element substantially abutting the resilient deformable grille element in the first position to restrict the passage of air through the abutting grille elements.

11. A dose indicator according to claim 10, wherein, when the indexing element is in the second position, the resilient deformable grille element is spaced from the further grille element to allow the passage of air through the spaced apart grille elements.

12. A dose indicator according to claim 10, wherein the further grille element is associated with one of: the display element and the chassis element.

13. A dose indicator according to claim 12, wherein the resilient deformable grille element is associated with the other one of: the display element and the chassis element.

14. A dose indicator according to any one of claim 9, wherein the chassis element comprises a housing including a base portion and a lid portion, the base portion including the indexing element and the resilient deformable grille element.

15. A dose indicator according to claim 14, wherein the lid portion is connected to the base portion by a living hinge.

16. A dose indicator according to claim 14, wherein the lid portion is closable with respect to the base portion.

17. A dose indicator according to claim 14, wherein the base portion comprises a wall portion having the viewing portion formed therein.

18. A dose indicator according to claim 9, wherein the chassis element comprises an inner wall portion and an outer wall portion joined by a rim portion, the inner and outer wall portions defining an annulus therebetween, the display element being mounted within the annulus with a portion thereof being visible through the viewing portion formed in the outer wall portion.

19. A pressure-actuated metered dispensing device comprising:
- an actuator portion;
- a window formed in the actuator portion;
- a dispensing portion;
- a nozzle block located between the actuator portion and the dispensing portion;
- a dose indicator according to any one of the preceding claims, the indexing element being aligned with the nozzle block and the viewing portion being aligned with the window in the actuator portion; and
- a canister comprising a container and a metering valve housed within the actuator portion, the metering valve having a valve stem that engages the nozzle block and wherein, in use, relative movement of the container and the nozzle block causes the translation of the indexing element from the first to the second position as a result of engagement of a portion of the canister and the indexing element.

\* \* \* \* \*